United States Patent [19]

Melvin

[11] Patent Number: 4,695,571
[45] Date of Patent: Sep. 22, 1987

[54] TRICYCLIC OXINDOLE ANTIINFLAMMATORY AGENTS

[75] Inventor: Lawrence S. Melvin, Ledyard, Conn.

[73] Assignee: Pfizer Inc., New York, N.Y.

[21] Appl. No.: 867,185

[22] PCT Filed: Aug. 24, 1984

[86] PCT No.: PCT/US84/01371
§ 371 Date: Apr. 2, 1986
§ 102(e) Date: Apr. 2, 1986

[87] PCT Pub. No.: WO86/01510
PCT Pub. Date: Mar. 13, 1986

[51] Int. Cl.⁴ .................... A61K 31/41; C07D 498/04; C07D 491/048; C07D 515/04
[52] U.S. Cl. .................... 514/275; 514/338; 514/363; 514/366; 514/367; 514/371; 514/372; 514/375; 514/377; 514/380; 514/411; 544/331; 546/270; 546/271; 546/272; 548/139; 548/151; 548/159; 548/181; 548/214; 548/218; 548/233; 548/246; 548/431; 548/450; 548/486
[58] Field of Search ............... 548/431, 218, 151, 450, 548/181, 233, 214, 246, 159, 139, 486; 544/331; 546/270, 271, 272; 514/411, 371, 338, 366, 375, 377, 372, 363, 380, 275, 367

[56] References Cited

U.S. PATENT DOCUMENTS 3,749,731 7/1973 Zinnes ................................ 548/431
4,644,005 2/1987 Melvin ................................ 514/338

Primary Examiner—Robert Gerstl
Attorney, Agent, or Firm—Peter C. Richardson; Albert E. Frost; James M. McManus

[57] ABSTRACT

Tricyclic oxindole carboxamides, prepared by (a) reaction of an isocyanate with the basic ring system or (b) ammonolysis of a corresponding alkyl ester, are nonsteroidal antiinflammatory agents useful in the treatment of rheumatoid arthritis.

25 Claims, No Drawings

TRICYCLIC OXINDOLE ANTIINFLAMMATORY AGENTS

TECHNICAL FIELD

Rheumatoid arthritis, which affects 3–4% of the population, is characterized by inflammation and pain of joints. Although the etiology of rheumatoid arthritis is not known both steroid and non-steroidal therapy have been employed to alleviate the symptoms of this illness. It is to this latter class of chemotherapeutic agents that the compounds of the present invention, namely tricyclic oxindole carboxamides, relate.

BACKGROUND ART

The potent non-steroidal antiinflammatory agent, Piroxicam, 4-hydroxy-2-methyl-N-(2-pyridyl)-2H-1,2-benzothiazine-3-carboxamide 1,1-dioxide was reported in U.S. Pat. No. 3,591,584. More recently, antiinflammatory activity was found in simple non-steroidal oxindole-3-carboxamides, U.S. Pat. No. 3,634,453.

DISCLOSURE OF INVENTION

In accordance with the present invention, it has now been found that a group of novel tricyclic oxindole carboxamide derivatives are useful as antiinflammatory agents.

The first group of compounds in this series are of the formulae:

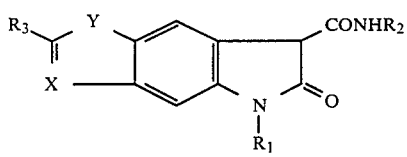

and

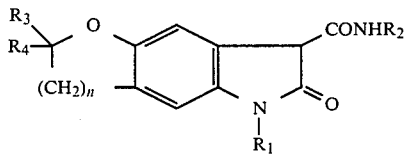

and the pharmaceutically acceptable base salts thereof, where Y is oxygen or sulfur; X is N, CH or C(CH$_3$); R$_1$ is alkyl of one to three carbon atoms or phenyl; R$_2$ is phenyl, monosubstituted phenyl the substituent being fluoro, chloro, trifluoromethyl, methylthio, methoxy, acetyl, ethoxycarbonyl or methylsulfinyl, disubstituted phenyl each substituent being fluoro or methoxy, or heterocyclic or mono or dimethyl heterocyclic where said heterocyclic is 2-thiazolyl, 2-oxazolyl, 5-isothiazolyl, 3-isoxazolyl, benzothiazolyl, 2-thiazolinyl, 2-thiadiazolyl, 2-pyrimidinyl or pyridyl; R$_3$ and R$_4$ are each hydrogen or methyl and n is an integer of 1 or 2.

Preferred within this first group are compounds of formula 1, where Y is oxygen, X is CH, R$_3$ is hydrogen and R$_1$ is alkyl as defined. Especially preferred are those compounds where R$_1$ is ethyl and R$_2$ is 2-thiazolyl, 4-methyl-2-thiazolyl, 4-fluorophenyl or 5-methyl-2-thiazolyl.

Also preferred are compounds of formula 1 where Y is sulfur, X is CH, R$_3$ is hydrogen and R$_1$ is alkyl as defined. Expecially preferred is the compound where R$_1$ is ethyl and R$_2$ is 5-methyl-2-thiazolyl.

Also preferred in this first group are compounds of formula 2 where R$_1$ is alkyl as defined, R$_3$ and R$_4$ are each hydrogen and n is 1. Especially preferred is the compound where R$_1$ is ethyl and R$_2$ is 4-fluorophenyl.

The second group of compounds of the present invention are of the formulae:

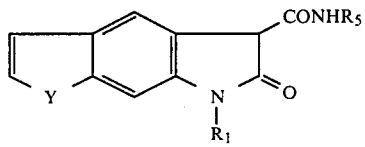

and

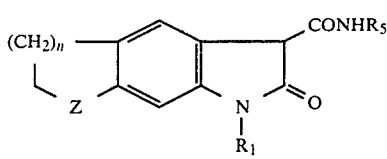

and the pharmaceutically acceptable base salts thereof, where Y is oxygen or sulfur; R$_1$ is alkyl of one to three carbon atoms or phenyl; Z is oxygen or methylene; n is an integer of 1 or 2; and R$_5$ is phenyl, fluorophenyl, difluorophenyl, chlorophenyl, pyridyl, 2-thiazolyl or monomethyl-2-thiazolyl.

Preferred within this second group are compounds of formula 3 where Y is oxygen and R$_1$ is alkyl as defined. Especially preferred are those compounds where R$_5$ is 5-methyl-2-thiazolyl or 2-thiazolyl and R$_1$ is ethyl.

Also preferred in this second group are compounds of formula 3 where Y is sulfur and R$_1$ is alkyl as defined. Especially preferred is the compound where R$_5$ is 5-methyl-2-thiazolyl and R$_1$ is ethyl.

The third type of compounds of interest are of the formula

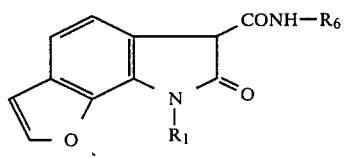

and the pharmaceutically acceptable base salts thereof, wherein R$_1$ is alkyl of one to three carbon atoms or phenyl and R$_6$ is fluorophenyl, difluorophenyl, pyridyl, 2-thiazolyl or 5-methyl-2-thiazolyl.

Preferred within this third group are compounds wherein R$_1$ is alkyl as defined. Especially preferred is the compound wherein R$_6$ is 5-methyl-2-thiazolyl and R$_1$ is ethyl.

Also claimed is a method of treating an inflammatory disease in a mammalian subject, which comprises administering to said mammalian subject an antiinflammatory disease treating amount of a compound of formula 1, 2, 3, 4 or 5 or pharmaceutically acceptable salt thereof wherein R$_1$ through R$_6$, n, X, Y and Z are as defined.

DETAILED DESCRIPTION

One of the processes employed in the preparation of the novel compounds of this invention consists of the interaction of an appropriate oxindole derivative with a requisite isocyanate as follows:

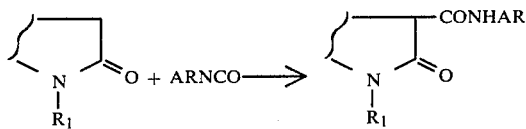

wherein $R_1$ is as defined and AR represents $R_2$, $R_5$ or $R_6$ as defined.

This reaction leading to the products of the instant invention is carried out in a reaction-inert solvent. Preferred solvents are polar, aprotic solvents such as dimethylformamide, diethylformamide, N-methyl-2-pyrrolidone or dimethylsulfoxide. Further it is preferred that the reaction be carried out in the presence of a base. Such bases include alkali and alkaline earth metal hydrides or a tertiary organic amine. The preferred base is sodium hydride.

In practice, the isocyanate is added to the oxindole derivative and base in the appropriate solvent. It is preferable to employ about a molar equivalent of the isocyanate and base, with best results achieved by using just a slight excess of each. It is preferred that the reagents be combined in the cold, generally from $-10°$ to $0°$ C., and that the reaction mixture be allowed to warm to room temperature. At from room temperature to $45°$ C. the reaction proceeds to completion in about a few minutes to overnight depending on the reactivity of the isocyanate.

Upon completion of the reaction, the product is isolated by addition the mixture to ice-water and treating with sufficient acid to provide a pH of between 2 and 5. The product can be filtered or extracted with a water immiscible solvent.

Purification can be by chromatography or by recrystallization from an appropriate solvent.

The oxindole starting reagents for this process are prepared by the herein described procedures. The requisite isocyanates are either commercially available or can be prepared by standard procedures known in the art, for instance, Zook and Wagner, Synthetic Organic Chemistry, John Wiley and Sons, Inc., New York, 1956, page 640.

A second reaction leading to the novel products of the present invention consists of the interaction of an appropriate amine with an oxindole ester as follows:

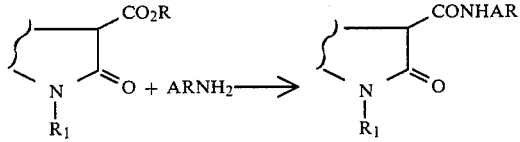

wherein $R_1$ is as defined, R is alkyl of one to four carbon atoms and AR is as defined.

This reaction leading to the products of the present invention is also carried out in a reaction-inert solvent. Preferred solvents are aprotic aromatic solvents such as benzene, toluene or xylene.

In practice, the reagents are combined in the appropriate solvent and heated to the reflux temperature of the solvent. It is preferable, in conducting this aminolysis reaction, to employ at least equimoles of ester and amine, although an excess of the amine, such as two equivalents, is especially preferred. To assist in removal of the alcohol by-product formed in the reaction a soxhlet containing molecular sieves is fitted to the reaction condenser. Using reflux temperatures of the solvents the reaction is generally complete in 45-60 minutes.

The product can be isolated by cooling the reaction mixture and filtering the product or by adding the reaction mixture to an acidified aqueous solution followed by extraction of the product and removal of the solvent.

Purification can be carried out by recrystallization of chromatography.

Starting reagents for the compounds of the present invention are either commercially available or can readily be prepared by the herein described procedures or procedures known to those skilled in the art.

It is noted that a common characteristic of many non-steroidal antiinflammatory agents is their acidic nature. Each of the oxindole carboxamides of the instant invention shares this property and is an effective proton source.

Pharmaceutically acceptable salts of the compounds of the present invention are also therapeutic agents, wherein the preferred cations of said salts include the ammonium, sodium and potassium ions. The pharmaceutically acceptable salts of the compounds described herein are prepared by conventional procedures, as for example, by adding the acid to an aqueous solution containing an equivalent amount of the pharmaceutically acceptable base, i.e., a base containing one of the above preferred cations, followed by concentration of the resultant mixture to obtain the desired product. The base can be selected from hydroxides, oxides or carbonates.

As previously indicated, the oxindole carboxamides of the present invention and their pharmaceutically acceptable salts are useful antiinflammatory agents. These compounds are of value in alleviating swelling and inflammation which are symptomatic of rheumatoid arthritis and related disorders which are responsive to treatment with antiinflammatory agents. Either as individual therapeutic agents or as mixtures of therapeutic agents, they may be administered alone, but are generally administered with a pharmaceutical carrier selected on the basis of the chosen route of administration and standard pharmaceutical practice. For example, they may be administered orally in the form of tablets or capsules containing such excipients as starch, milk sugar or certain types of clay, etc. They may be administered orally in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitable buffered, if necessary, and should contain other solutes such as saline or glucose to render them isotonic.

The dosage required to reduce inflammation or swelling in arthritic subjects would be determined by the nature and extent of the symptoms. Generally, small doses will be required initially, with a gradual increase in the dose until the optimum level is determined. It will generally be found that when the composition is administered orally, larger amounts of the active ingredient will be required to produce the same level as produced by a smaller quantity administered parenterally. In general, from about 10 to about 300 mg. of active ingredient per kilogram of body weight, administered orally in single or multiple dose units, will effectively reduce inflammation and swelling.

A standard procedure for detecting and comparing antiinflammatory activity of compounds is the carrageenin rat foot edema test, which is described by C. A. Winter et al., Proc. Soc. Exp. Biol., vol III, page 544 (1962).

In addition to being useful as antiinflammatory agents, the compounds of the present invention can be used in the treatment of asthma, bronchitis and psoriasis; they can also be used as analgesic agents.

The following examples are provided solely for the purpose of further illustration. Nuclear magnetic resonance spectra (NMR) were measured at 60 MHz for solutions in deuterochloroform ($CDCl_3$), perdeutero dimethyl sulfoxide (DMSO-$d_6$) or deuterium oxide ($D_2O$) or are noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; d, doublet, t, triplet; q, quartet; m, multiplet; b, broad.

EXAMPLE 1

N-(4-Chlorophenyl)-5-ethyl-6-oxo-2,3,6,7-tetrahydrofuro[2,3-f]indole-7-carboxamide (2, $R_1=C_2H_5$, $R_2=$4-chlorophenyl, $R_3$ and $R_4=H$ and $n=1$)

To a slurry of 18 mg. (0.803 mmole) of sodium hydride in 740 ul. of dimethylformamide cooled to $-10°$ C. was added 150 mg. (0.739 mmole) of 5-ethyl-6-oxo-2,3,6,7-tetrahydro-furo[2,3-f]indole. After the evolution of gas ceased, 125 mg. (0.813 mmole) of 4-chlorophenylisocyanate was added and the reaction mixture allowed to warm to 25° C. and stir for 16 hours. The reaction mixture was poured into a saturated solution of sodium chloride—1N hydrochloric acid and extracted with ethyl acetate. The extract was dried over magnesium sulfate and concentrated to dryness in vacuo. The residue was purified by chromatographing on 20 g. of silica gel using ethyl acetate-hexane (1:2, v:v) as the eluant. The final product was recrystallized from diethyl etherdichloromethane, 15 mg. (6% yield), m.p. 175°–176° C.

The NMR ($CDCl_3$) spectrum showed absorption at 1.25 (J=6 Hz, $CH_3$), 3.19 (J=8 Hz, $CH_2$), 3.74 (J=6 Hz, $NCH_2$), 4.25 (CH), 4.53 (J=8 Hz, $OCH_2$), 6.70 (2 ArH), 7.1–7.7 (4 ArH) and 9.67 (NH) ppm.

EXAMPLE 2

N-(4-Fluorophenyl)-2-methyl-5-ethyl-6-oxo-2,3,6,7-tetrahydro-furo[2,3-f]indole-7-carboxamide (2, $R_1=C_2H_5$, $R_2=$4-fluorophenyl, $R_3=CH_3$ $R_4=H$ and $n=1$)

Following the procedure of Example 1 and employing 326 mg. (1.5 mmoles) of 2-methyl-5-ethyl-6-oxo-2,3,6,7-tetrahydrofuro[2,3-f]indole and 0.24 ml. (2.1 mmoles) of 4-fluorophenylisocyanate, 240 mg. (45% yield), m.p. 196°–197° C. of the desired product was obtained.

Anal. Calcd. for $C_{20}H_{19}FO_3N_2$: C, 67.8; H, 5.4; N, 7.9. Found: C, 67.7; H, 5.5; N, 8.0.

The NMR spectrum ($CDCl_3$) showed absorption at 1.28 (J=7 Hz, $CH_3$), 1.43 (J=6 Hz, $CH_3$), 2.5–3.4 ($CH_2$), 3.75 (J=7 Hz, $NCH_2$), 4.25 (CH), 4.90 (J=6 Hz), 6.6–7.6 (ArH) and 9.57 (NH) ppm.

EXAMPLE 3

N-(5-Methylthiazo-2-yl)-5-ethyl-6-oxo-6,7-dihydro-furo[2,3-f]indole-7-carboxamide (1, $R_1=C_2H_5$, $R_2=$5-methylthiazo-2-yl, $R_3=H$, X=CH and Y=O)

A solution of 12.4 g. (45.2 mmoles) of ethyl 5-ethyl-6-oxo-6,7-dihydro-furo[2,3-f]indole-7-carboxylate and 10.3 g. (90.5 mmoles) of 2-amino-5-methylthiazole in 452 ml. of benzene was heated at reflux for 45 minutes with the reaction condenser fitted with a soxhlet filled with 4A molecular sieves. The reaction mixture was then added to 1 l. of dichloromethane and 500 ml. of ice cold 1N hydrochloric acid. The organic layer was separated, dried over magnesium sulfate and concentrated under vacuum. The residue was recrystallized from dichloromethane, 11.3 g. (73% yield), m.p. 196°–201° C.

The NMR ($CDCl_3$) spectrum showed absorption at 1.32 (J=7 Hz, $CH_3$), 2.39 (J=1 Hz, $CH_3$), 3.83 (J=7 Hz, $NCH_2$), 4.45 (CH), 6.61 (ArH), 7.02 (ArH), 7.60 (J=2 Hz, ArH) and 7.92 (CH thiazole) ppm.

Anal. Calcd. for $C_{17}H_{15}O_3N_3S$: C, 59.8; H, 4.4; N, 12.3. Found: C, 59.6; H, 4.5; N, 12.5.

EXAMPLE 4

Employing the procedure of Example 3 and starting with the appropriate ester and amine, the following compounds were prepared:

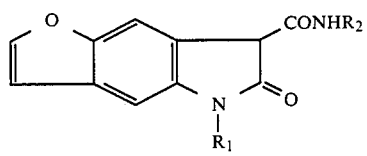

| $R_1$ | $R_2$ | m.p., °C. | NMR ($CDCl_3$) delta |
|---|---|---|---|
| n-$C_3H_7$ | ![thiazole with CH3 on S side] | 118–125 | 0.98 (J=7Hz, $CH_3$), 1.75 (J=7Hz, $CH_2$), 2.36 ($CH_3$), 3.74 (J=7Hz, $NCH_2$), 6.7 (ArH), 7.07 (ArH), 7.02 (ArH), 7.58 J=2Hz, ArH) and 7.87 (CH) |
| $CH_3$ | ![thiazole with CH3 on S side] | 193–195 | 2.4 ($CH_3$), 3.32 ($NCH_3$), 6.78 (ArH), 7.05 (ArH) and 7.62 (ArH) |

|  |  | -continued |  |
|---|---|---|---|
| C₂H₅ | 3-methyl-5-methyl-isoxazole-like (O, N, CH₃) | 172–182 | 1.29 (J=7Hz, CH₃), 2.42 (CH₃), 3.95 (J=7Hz, NCH₂), 6.70 (ArH), 7.0 (ArH), 7.52 (ArH) and 8.10 (ArH). |
| C₂H₅ | 3-methyl-isothiazole (S, N, CH₃) | 192–197 | (CDCl₃—DMSO—d₆), 1.32 (J=7Hz, CH₃), 2.42 (CH₃), 3.92 (J=7Hz, NCH₂), 6.75 (ArH), 6.79 (J=2Hz, ArH), 7.07 (ArH), 7.61 (J=2Hz, ArH) and 7.67 (ArH). |
| C₂H₅ | phenyl | 195–197 | 1.29 (J=7Hz, CH₃), 3.89 (J=7Hz, NCH₂), 4.40 (CH), 6.64 (ArH), 7.0–7.6 (ArH), and 7.92 (ArH). |
| C₂H₅ | 2,5-dimethylbenzothiazole | 191–194 | (CDCl₃—DMSO—d₆), 1.29 (J=7Hz, CH₃), 2.79 (CH₃), 3.89 (J=7Hz, NCH₂), 4.69 (CH), 6.76 (ArH), 7.02 (ArH), 7.62 (ArH) and 8.22 (ArH). |
| C₂H₅ | 4-(methylthio)phenyl (SCH₃) | 180–181 | 1.3 (J=7Hz, CH₃), 2.50 (CH₃), 3.88 (J=7Hz, NCH₂), 4.42 (CH), 6.72 (ArH), 7.0–7.6 (ArH) and 7.92 (ArH). |
| C₂H₅ | 4-(trifluoromethyl)phenyl (CF₃) | 157–159 | 1.32 (J=7Hz, CH₃), 3.89 (J=7Hz, NCH₂), 4.42 (CH), 6.7 (ArH), 7.0 (ArH), 7.59 (ArH) and 7.91 (ArH). |
| C₂H₅ | 4-fluorophenyl (F) | 150–152 | 1.32 (J=7Hz, CH₃), 3.89 (J=7Hz, NCH₂), 4.42 (CH), 6.74 (ArH), 6.8–7.3 (ArH), 7.4–7.7 (ArH) and 7.99 (ArH). |
| C₂H₅ | 3-methyl-5-methylisoxazole (N, O, CH₃) | 176–177 | 1.32 (J=7Hz, CH₃), 2.4 (CH₃), 3.95 (J=7Hz, NCH₂), 4.41 (CH), 6.61 (ArH), 6.71 (ArH), 7.01 (ArH), 7.6 (J=2Hz, ArH), 7.84 (ArH) and 10.11 (NH). |
| C₂H₅ | 2-methyl-4-methylthiazole (S, N, CH₃) | 165–170 | (CDCl₃—DMSO—d₆), 1.29 (J=7Hz, CH₃), 2.32 (CH₃), 3.90 (J=7Hz, NCH₂), 6.46 (ArH), 6.63 (ArH), 7.01 (ArH) and 7.60 (ArH). |
| C₂H₅ | pyridin-2-yl (N) | 209–211 | Calcd. for C₁₈H₁₅O₃N₃·¼H₂O: C, 66.4; H, 4.8; N, 12.9, Found: C, 66.2; H, 4.7; N, 12.8. |
| C₂H₅ | 2-methylbenzothiazole (S, N) | 165–170 | (CDCl₃—DMSO—d₆) 1.22 (J=7Hz, CH₃), 3.95 (J=7Hz, NCH₂), 6.9 (ArH) and 7.1–8.1 (ArH). |

-continued

| | | | |
|---|---|---|---|
| C₂H₅ | 4,5-dimethylthiazol-2-yl | 210–215 | Calcd. for C₁₈H₁₇O₃N₃S.H₂O: C, 57.9; H, 5.1; N, 11.3. Found: C, 57.6; H, 4.7; N, 11.0 |
| C₂H₅ | 2,4-difluorophenyl | 158–161 | 1.29 (J=7Hz, CH₃), 3.89 (J=7Hz, NCH₂), 4.5 (CH), 6.6–7.1 (ArH), 7.62 (J=2Hz, ArH), 7.98 (ArH), 8.3 (ArH) and 9.98 (NH). |
| C₂H₅ | thiazol-2-yl | 180–185 | (CDCl₃—DMSO—d₆) 1.29 (J=7Hz, CH₃), 3.83 (J=7Hz, NCH₂), 6.73 (ArH), 6.98 (ArH), 7.40 (J=4Hz, ArH) and 7.61 (ArH). |
| C₂H₅ | thiazol-2-yl | 185–195 | Calcd. for C₁₆H₁₅O₃N₃S: C, 58.4; H, 4.6; N, 12.8. Found: C, 58.2; H, 4.6; N, 12.6. |
| C₂H₅ | 1,3,4-thiadiazol-2-yl | 237–238 | (CDCl₃—DMSO—d₆) 1.3 (J=7Hz, CH₃), 3.89 (J=7Hz, CH₂), 6.85 (J=2Hz, ArH), 7.2 (ArH), 7.79 (J=2Hz, ArH) and 8.09 (ArH). |
| C₂H₅ | 4,6-dimethylpyrimidin-2-yl | 242–244 | HRMS (M/e) Calcd: 350.1379. Found: 350.1380. |
| C₂H₅ | 6-methylpyridin-2-yl | 225–227 | HRMS (M/e) Calcd: 335.1269. Found: 335.1253. |
| C₂H₅ | 3-trifluoromethylphenyl | 160–162 | 1.36 (J=7Hz, CH₃), 3.96 (J=7Hz, NCH₂), 4.46 (CH), 6.80 (J=2Hz, ArH), 7.05 (ArH), 7.2–8.0 (ArH) and 9.93 (NH). |
| C₂H₅ | 5-trifluoromethyl-1,3,4-thiadiazol-2-yl | 180–190 | (CDCl₃—DMSO—d₆), 1.29 (J=7Hz, CH₃), 3.90 (J=7Hz, NCH₂), 6.8 (ArH), 7.10 (ArH), 7.52 (ArH) and 7.67 (J=2Hz, ArH). |
| C₂H₅ | 5-methyl-1,3,4-thiadiazol-2-yl | 242–243 | (CDCl₃—DMSO—d₆) 1.29 (J=7Hz, CH₃), 2.65 (CH₃), 3.84 (J=7Hz, NCH₂; 6.8 (ArH), 7.12 (ArH), 7.52 (ArH) and 7.7 (ArH). |
| C₂H₅ | 5-ethyl-1,3,4-thiadiazol-2-yl | 210–212 | HRMS (M/e) Calcd.: 356.0943. Found: 356.0929. |

-continued

| | | | | | 253 | (DMSO—d6 + NaOD) 2.31 (CH3), 6.72 (ArH), 6.96 (ArH), 7.37 (ArH), 7.5 (ArH), 7.6 (J=2Hz, ArH) and 7.84 (CH). |

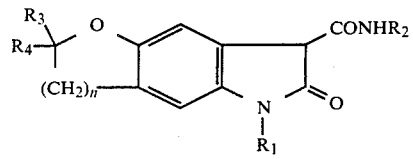

| R1 | R2 | R3 | R4 | n | m.p. °C. | NMR (CDCl3)delta |
|---|---|---|---|---|---|---|
| C2H5 | (N-thiazolyl with CH3) | CH3 | CH3 | 1 | 129–131 | 1.22 (J=7Hz, CH3), 1.44 (CH3), 2.36 (J=1Hz, CH3), 3.74 (J=7Hz, NCH2), 4.38 (CH), 6.69 (ArH), 7.05 (ArH) and 7.17 (ArH). |
| C2H5 | (N-thiazolyl with CH3) | H | H | 1 | 200–207 | (CDCl3—DMSO—d6 1.20 (J=7Hz, CH3), 2.31 (J=1Hz, CH3), 3.15 (J=8Hz, CH2), 3.68 (J=7Hz, NCH2), 4.44 (J=8Hz, CH2O), 6.8 (ArH) and 6.98 (J=1Hz, CH). |
| C2H5 | 4-F-phenyl | H | H | 1 | 176–178 | 1.3 (J=7Hz, CH3), 3.2 (J=8Hz, CH2), 3.78 (J=7Hz, CH2), 4.29 (CH), 4.57 (J=8Hz, OCH2), 6.73 (ArH), 6.98 (J=1 and 8, ArH), 7.28 (ArH) and 7.52 (J=9 and 5Hz, ArH). |
| C2H5 | 2,4-diF-phenyl | H | H | 1 | 184–186 | 1.29 (J=7Hz, CH3), 3.2 (J=8Hz, CH2), 3.79 (J=7Hz, NCH2), 4.32 (CH), 4.58 (J=8Hz, OCH2), 6.8–7.1 (ArH), 7.22 and 8.2 (ArH). |
| C2H5 | 2-F-phenyl | H | H | 1 | 192–194 | 1.29 (J=7Hz, CH3), 3.2 (J=8Hz, CH2), 3.79 (J=7Hz, NCH2), 4.55 (CH), 4.57 (J=8Hz, OCH2), 6.71 (ArH), 7.0 (ArH), 7.27 (ArH) and 8.25 (ArH). |
| C2H5 | 3-F-phenyl | H | H | 1 | 180–182 | 1.29 (J=7Hz, CH3), 3.20 (J=8Hz, CH2), 3.75 (J=7Hz, NCH2), 4.29 (CH), 4.56 (J=8Hz, OCH2) and 6.5–7.7 (ArH). |

| | | | | | | |
|---|---|---|---|---|---|---|
| | | | | | -continued | |
| C₂H₅ | 2,6-difluorophenyl | H | H | 1 | 220-226 | 1.30 (J=7Hz, CH₃), 3.2 (J=8Hz, CH₂), 3.73 (J=7Hz, NCH₂), 4.42 (CH), 4.56 (J=8Hz, OCH₂) and 6.6-7.4 (ArH). |
| C₂H₅ | 4-OCH₃-phenyl | H | H | 1 | 186-187 | 1.29 (J=7Hz, CH₃), 3.18 J=8Hz, CH₂), 3.79 (J=7Hz, NCH₂), 3.79 (OCH₂), 4.29 (CH), 4.56 (J=8Hz, OCH₂), 6.8 (J=8Hz, ArH), 7.25 (ArH) and 7.45 (J=8Hz, ArH). |
| C₂H₅ | phenyl | H | H | 1 | 210-212 | (CDCl₃—DMSO—d₆) 1.29 (J=7Hz, CH₃), 3.22 (J=8Hz, CH₂), 3.79 (J=7Hz, CH₂), 4.5 (CH), 4.57 J=8Hz, OCH₂), 6.7-7.7 (ArH) and 9.93 (NH). |
| C₂H₅ | 3-OCH₃-phenyl | H | H | 1 | 170-171.5 | 1.29 (J=7Hz, CH₃), 3.2 (J=8Hz, CH₂), 3.78 (J=7Hz, NCH₂), 3.81 (OCH₂), 4.3 (CH), 4.57 (J=8Hz, OCH₂), 6.5-7.5 (ArH) and 9.83 (NH). |
| C₂H₅ | 2,5-difluorophenyl | H | H | 1 | 218-222 | 1.28 (J=7Hz, CH₃), 3.2 (J=8Hz, CH₂), 3.8 (J=7Hz, NCH₂), 4.48 (CH), 4.52 (J=8Hz, OCH₂), 6.5-7.4 (ArH), 8.1 (ArH) and 10.13 (NH). |
| C₂H₅ | 2-OCH₃-phenyl | H | H | 1 | 189-191 | 1.28 (J=7Hz, CH₃), 3.2 (J=8Hz, CH₂), 3.76 (J=7Hz, NCH₂), 3.96 (OCH₂), 4.35 (CH), 4.53 (J=8Hz, OCH₂), 6.7-7.4 (ArH), 8.35 (ArH) and 10.0 (NH). |
| C₂H₅ | 4-CF₃-phenyl | H | H | 1 | 184-185 | 1.3 (J=7Hz, CH₃), 3.20 (J=8Hz, CH₂), 3.8 (J=7Hz, NCH₂), 4.32 (CH), 4.58 (J=8Hz, OCH₂), 6.77 (ArH), 7.28 (ArH), 7.5 (J=8.5Hz, ArH), 7.74 (J=8.5Hz, ArH) and 9.93 (NH). |

-continued

| | | | | | | |
|---|---|---|---|---|---|---|
| C$_2$H$_5$ | 3-(CO-OCH$_3$)-C$_6$H$_4$— | H | H | 1 | 169–171 | 1.29 (J=7Hz, CH$_3$), 2.6 (COCH$_3$), 3.2 (J=8Hz, CH$_2$), 3.79 (J=7Hz, NCH$_2$), 4.32 (CH), 4.57 (J=8Hz, OCH$_2$), 6.72 (ArH), 7.2–7.7 (ArH), 7.82 (ArH) and 8.1 (ArH). |
| C$_2$H$_5$ | 4-(SCH$_3$)-C$_6$H$_4$— | H | H | 1 | 197–198 | 1.29 (J=7Hz, CH$_3$), 2.46 (SCH$_3$), 3.21 (J=8Hz, CH$_2$), 3.78 (J=7Hz, NCH$_2$), 4.28 (CH), 4.56 (J=8Hz, OCH$_2$), 6.72 (ArH), 7.2 (J=8Hz, ArH), 7.27 (ArH) and 7.52 (J=8Hz, ArH). |
| C$_2$H$_5$ | 4-(COCH$_3$)-C$_6$H$_4$— | H | H | 1 | 228–230 | (CDCl$_3$—DMSO—d$_6$), 1.23 (J=7Hz, CH$_3$), 2.54 (COCH$_3$), 3.3 (CH$_2$), 3.80 (J=7Hz, NCH$_2$), 4.50 (J=8Hz, OCH$_2$), 4.60 (CH), 6.83 (ArH), 7.67 (J=8Hz, ArH), 7.88 (ArH) and 10.6 (NH). |
| C$_2$H$_5$ | 3-(CF$_3$)-C$_6$H$_4$— | H | H | 1 | 176–178 | 1.31 (J=7Hz, CH$_3$), 3.2 (J=8Hz, CH$_2$), 3.79 (J=7Hz, NCH$_2$), 4.32 (CH), 4.57 (J=8Hz, OCH$_2$), 6.72 (ArH), 7.2–8.0 (ArH) and 9.87 (NH). |
| C$_2$H$_5$ | 2-(COCH$_3$)-C$_6$H$_4$— | H | H | 1 | 238–239 | (CDCl$_3$—DMSO—d$_6$), 1.28 (J=7Hz, CH$_3$), 3.18 (COCH$_3$), 3.18 (CH$_2$), 3.80 (NCH$_2$), 4.42 (J=8Hz, OCH$_2$), 6.9–7.6 (ArH) and 10.57 (NH). |
| C$_2$H$_5$ | 2-(CF$_3$)-C$_6$H$_4$— | H | H | 1 | 147–149 | 1.29 (J=7Hz, CH$_3$), 3.22 J=8Hz, CH$_2$), 3.79 (J=7Hz, NCH$_2$), 4.37 (CH), 4.59 (J=8Hz, OCH$_2$), 6.73 (ArH), 7.1–7.8 (ArH), 8.2 (J=8Hz, ArH) and 9.67 (NH). |

|   |   |   |   |   |   |   |
|---|---|---|---|---|---|---|
| | -continued | | | | | |
| $C_2H_5$ | 3-($C_2H_5O$-C(=O))-phenyl | H | H | 1 | 163–165 | 1.3 (J=7Hz, $CH_3$), 1.4 (J=7Hz, $CH_3$), 3.21 (J=8Hz, $CH_2$), 3.79 (J=7Hz, $NCH_2$), 4.38 (J=7Hz, $OCH_2$), 4.31 (CH), 4.58 (J=8Hz, $OCH_2$), 6.72 (ArH), 7.2–8.2 (ArH) and 9.83 (NH). |
| $C_2H_5$ | 4-($C_2H_5O$-C(=O))-phenyl | H | H | 1 | 193–197 | 1.30 (J=7Hz, $CH_3$), 1.40 (J=7Hz, $CH_3$), 3.22 (J=8Hz, $CH_2$), 3.79 (J=7Hz, $NCH_2$), 4.32 (J=7Hz, $OCH_2$), 4.32 (CH), 4.59 (J=8Hz, $OCH_2$), 6.72 (ArH), 7.25 (ArH), 7.64 (J=8Hz, ArH), 8.0 J=8Hz, ArH) and 9.93 (NH). |
| $C_2H_5$ | 2-($C_2H_5O$-C(=O))-phenyl | H | H | 1 | 193–197 | 1.29 (J=7Hz, $CH_3$), 1.41 (J=7Hz, $CH_3$), 3.21 (J=8Hz, $CH_2$), 3.79 (J=7Hz, $NCH_2$), 4.41 (J=7Hz, $OCH_2$), 4.42 (CH), 4.57 (J=7Hz, $OCH_2$), 6.72 (ArH), 6.9–7.7 (ArH), 8.02 (J=8Hz, ArH) and 8.63 and 8.77 (NH). |
| $C_2H_5$ | 3-F-4-$OCH_3$-phenyl | H | H | 1 | 181–183 | 1.29 (J=7Hz, $CH_3$), 3.21 (J=8Hz, $CH_2$), 3.80 (J=7Hz, $NCH_2$), 3.85 ($OCH_2$), 4.3 (CH), 4.59 (J=8Hz, $OCH_2$), 6.72 (ArH), 6.90 (J=8Hz, ArH), 7.19 (J=8Hz, ArH), 7.25 (ArH), 7.49 (J=12Hz, ArH) and 9.60 (NH). |
| $C_2H_5$ | 3-$SCH_3$-phenyl | H | H | 1 | 130–132 | 1.29 (J=7Hz, $CH_3$), 2.46 ($SCH_3$), 3.2 (J=8Hz, $CH_2$), 3.75 (J=7Hz, $NCH_2$), 4.28 (CH), 4.55 (J=8Hz, $OCH_2$), 6.7 (ArH), 6.9–7.4 (ArH), 7.54 (ArH) and 9.83 (NH). |

| | | | | | | |
|---|---|---|---|---|---|---|
| C$_2$H$_5$ | 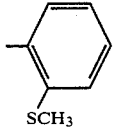 | H | H | 1 | 125–128 | 1.29 (J=7Hz, CH$_3$), 2.41 (SCH$_3$), 3.21 (J=8Hz, CH$_2$), 3.79 (J=7Hz, NCH$_2$), 4.4 (CH), 4.55 (J=8Hz, OCH$_2$), 6.71 (ArH), 6.8–7.5 (ArH), 8.2 (J=8Hz, ArH) and 10.17 (NH). |
| C$_2$H$_5$ | 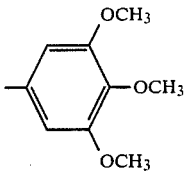 | H | H | 1 | 174–175 | 1.29 (J=7Hz, CH$_3$), 3.21 (J=8Hz, CH$_2$), 3.82 (OCH$_2$), 3.85 (OCH$_3$), 4.31 (CH), 4.58 (J=8Hz, OCH$_2$), 6.75 (ArH), 6.9 (ArH) and 7.25 (ArH). |
| C$_2$H$_5$ | 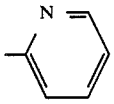 | H | H | 1 | 228–230 | (DMSO—d$_6$-NaOD) 1.18 (J=7Hz, CH$_3$), 3.12 (J=8Hz, CH$_2$), 3.80 (J=7Hz, NCH$_2$), 4.40 (J=8Hz, OCH$_2$), 6.6–7.8 (ArH) 8–8.3 (ArH). |

EXAMPLE 5

N-(4-Methylsulfinylphenyl)-5-ethyl-6-oxo-2,3,6,7-tetrahydro-furo[2,3-f]indole-7-carboxamide (2, R$_1$=C$_2$H$_5$, R$_2$=4-methylsulfinylphenyl, R$_3$ and R$_4$=H and n=1)

To 500 mg. (1.36 mmoles) of N-(4-methylthiophenyl)-5-ethyl-6-oxo-2,3,6,7-tetrahydro-furo[2,3-f]indole-7-carboxamide in 10 ml. of dichloromethane cooled to −5° C. was added 292 mg. (1.7 mmoles) of m-chloroperbenzoic acid. The reaction mixture was allowed to stir for 30 minutes and was then added to 200 ml. of a saturated aqueous solution of sodium bicarbonate and 200 ml. of dichloromethane.

The organic phase was separated and saved, and the aqueous layer extracted with additional dichloromethane (2×50 ml.). The organic extracts were combined, dried over magnesium sulfate and concentrated to dryness. The residual product was purified by recrystallization from dichloromethane-diisopropyl ether, 319 mg. (61% yield), m.p. 204°–205° C.

The NMR spectrum (CDCl$_3$) showed absorption at 1.29 (J=7 Hz, CH$_3$), 2.70 (SOCH$_3$), 3.22 (J=8 Hz, CH$_2$), 3.80 (J=7 Hz, NCH$_2$), 4.32 (CH), 4.59 (J=8 Hz, OCH$_2$), 6.71 (ArH), 7.25 (ArH), 7.52 (J=8.5 Hz, ArH) and 7.78 (J=8 Hz, ArH) ppm.

In a similar manner, 400 mg. (1.09 mmoles) of N-(3-methylthiophenyl)-5-ethyl-6-oxo-2,3,6,7-tetrahydrofuro[2,3-f]indole-7-carboxamide and 224 mg. (1.3 mmoles) of m-chloroperbenzoic acid gave 390 mg. (94% yield) of N-(3-methylsulfinylphenyl)-5-ethyl-6-oxo-2,3,6,7-tetrahydro-furo[2,3-f]indole-7-carboxamide, m.p. 180°–185° C.

The NMR spectrum (CDCl$_3$) showed absorption at 1.32 (J=7 Hz, CH$_3$), 2.71 (SOCH$_3$), 3.21 (J=8 Hz, CH$_2$), 3.79 (J=7 Hz, NCH$_2$), 4.33 (CH), 4.59 (J=8 Hz, OCH$_2$), 6.74 (ArH), 7.2–8.0 (ArH) and 9.93 (NH).

Again, following the procedure of Example 5, 400 mg. (1.09 mmoles) of N-(2-methylthiophenyl)-5-ethyl-6-oxo-2,3,6,7-tetrahydro-furo[2,3-f]indole-7-carboxamide and 224 mg. (1.3 mmoles) of m-chloroperbenzoic acid gave 290 mg. (70% yield) of N-(2-methylsulfinylphenyl)-5-ethyl-6-oxo-2,3,6,7-tetrahydro-furo[2,3-f]indole-7-carboxamide, m.p. 137°–138° C.

The NMR spectrum (CDCl$_3$) showed absorption at 1.30 (J=7 Hz, CH$_3$), 2.85 and 2.98 (SOCH$_3$), 3.23 (J=8 Hz, CH$_2$), 3.79 (J=7 Hz, NCH$_2$), 4.4 (CH), 4.59 (J=8 Hz, OCH$_2$), 6.78 (ArH), 7.0 and 7.06 (ArH), 7.1–7.6 (ArH), 8.1–8.4 (ArH) and 10.27 and 10.6 (NH) ppm.

EXAMPLE 6

Employing the procedure of Example 1, and starting with 500 mg. (2.16 mmoles) of 2,2-dimethyl-5-ethyl-6-oxo-2,3,6,7-tetrahydro-furo[2,3-f]indole and 0.34 ml. (2.99 mmoles) of 4-fluorophenylisocyanate, 493 mg. (62% yield) of N-(4-fluorophenyl)-2,2-dimethyl-5-ethyl-6-oxo-2,3,6,7-tetrahydro-furo[2,3-f]indole-7-carboxamide (2, R$_1$=C$_2$H$_5$, R$_2$=4-fluorophenyl, R$_3$ and R$_4$=CH$_3$, and n=1) m.p. 160°–162° C., was obtained.

The NMR spectrum (CDCl$_3$) showed absorption at 1.22 (J=7 Hz, CH$_3$), 1.41 and 1.45 (CH$_3$), 2.99 (CH$_2$), 3.72 (J=7 Hz, NCH$_2$), 4.29 (CH), 6.7–7.7 (ArH) and 9.60 (NH) ppm.

EXAMPLE 7

N-(5-Methylthiazo-2-yl)-2-methyl-5-ethyl-6-oxo-6,7-dihydro-furo[2,3-f]indole-7-carboxamide (1, R$_1$=C$_2$H$_5$, R$_2$=5-methylthiazo-2-yl, R$_3$=CH$_3$, X=CH and Y=O)

A solution of 1.0 g. (3.48 mmoles) of ethyl 2-methyl-5-ethyl-6-oxo-furo[2,3-f]indole-7-carboxylate and 793 mg. (6.96 mmoles) of 2-amino-5-methylthiazole in 35 ml. of benzene was heated at reflux for 45 minutes with the reaction condenser fitted with a soxhlet filled with 4A molecular sieves. After the indicated period of time the reaction mixture was added to a mixture of 145 ml. of dichloromethane and 150 ml. of ice cold 1N hydrochloric acid. The organic layer was separated, dried over magnesium sulfate and concentrated in vacuo. The residual product was recrystallized from dichloromethane—diisopropyl ether, 1.06 g. (85% yield), m.p. 170°–175° C.

The NMR spectrum (CDCl₃) showed absorption at 1.32 (J=7 Hz, CH₃), 2.4 (J=1 Hz, CH₃), 2.48 (J=1 Hz, CH₃), 3.85 (J=7 Hz, CH₂), 4.5 (CH), 6.34 (ArH), 6.9 (ArH), 7.05 (ArH) and 7.8 (CH) ppm.

Anal. Calcd. for $C_{18}H_{17}O_3N_3S$: C, 60.8; H, 4.8; N, 11.8. Found: C, 60.7; H, 5.1; N, 11.6.

EXAMPLE 8

Following the procedure of Example 7, and employing the appropriate reagents, the indicated compounds were prepared:

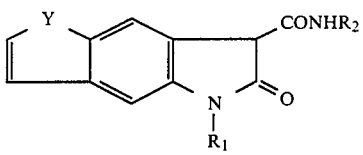

| R₁ | R₂ | Y | m.p. °C. | NMR (CDCl₃) delta |
|---|---|---|---|---|
| C₂H₅ | (2-(5-methylthiazol-2-yl)) | S | 225–227 | 1.22 (J=7Hz, CH₃), 2.32 (J=1Hz, CH₃), 3.84 (J=7Hz, NCH₂), 5.0 (CH), 7.2–7.6 (ArH) and 7.99 (ArH). |
| C₂H₅ | (3,4-difluorophenyl) | S | 216–219 | 1.2 (J=7Hz, CH₃), 3.77 (J=7Hz, NCH₂), 4.71 (CH), 6.9–7.9 (ArH) and 8.0 (ArH). |

EXAMPLE 9

N-(5-Methylthiazo-2-yl)-2-methyl-5-ethyl-6-oxo-6,7-dihydro-oxazolo[5,4-f]indole-7-carboxamide (1, R₁=C₂H₅, R₂=5-methylthiazo-2-yl, R₃=CH₃, X=N and Y=O)

A benzene (12 ml.) solution of 337 mg. (1.17 mmoles) of ethyl 2-methyl-5-ethyl-6-oxo-6,7-dihydrooxazolo[5,4-f]indole-7-carboxylate and 267 mg. (2.34 mmoles) of 2-amino-5-methylthiazole was heated to reflux through a soxhlet filled with 4A molecular sieves for 45 minutes. The reaction mixture was cooled and the precipitated product was filtered, washed with benzene and dried, 451 mg. The product was partitioned between dichloromethane and 1N hydrochloric acid solution. The organic was separated, dried over magnesium sulfate and concentrated to a small volume. n-Hexane was added to precipitate the product, 150 mg., m.p. 178° C. (dec.)

Anal. Calcd. for $C_{17}H_{16}O_3NS$: C, 57.3; H, 4.5; N, 15.7. Found: C, 56.9; H, 4.9; N, 15.4.

The NMR spectrum (d₆-DMSO) showed absorption at 1.2 (J=8 Hz, CH₃), 2.58 (CH₃), 3.9 (CH₂, CH), 7.19 (ArH), 7.39 (ArH) and 13.7 (NH) ppm.

EXAMPLE 10

N-(5-Methylthiazo-2-yl)-5-ethyl-6-oxo-6,7-dihydro-furo[3,2-f]indole-7-carboxamide (3, R₁=C₂H₅, R₅=5-methylthiazo-2-yl, Y=O)

A solution of 500 mg. (1.83 mmoles) of ethyl 5-ethyl-6-oxo-6,7-dihydro-furo[3,2-f]indole-7-carboxylate and 417 mg. (3.66 mmoles) of 2-amino-5-methylthiazole in 20 ml. of benzene was heated to reflux for 45 minutes with the reaction condenser fitted with a soxhlet filled with 4A molecular sieves. The reaction mixture was then added to 150 ml. of dichloromethane and 150 ml. of ice cold 1N hydrochloric acid. The organic phase was separated, dried over magnesium sulfate and concentrated to dryness. Recrystallization of the residual product from dichloromethane diisopropyl ether gave 474 mg. (76% yield) of the desired compound, m.p. 194°–196° C.

Anal. Calcd. for $C_{17}H_{15}O_3N_3S$: C, 59.8; H, 4.4; N, 12.3. Found: C, 59.5; H, 4.7; N, 12.1.

The NMR spectrum (CDCl₃) showed absorption at 1.32 (J=7 Hz, CH₃), 2.4 (CH₃), 3.85 (J=7 Hz, NCH₂), 4.45 (CH), 6.77 (ArH), 7.52 (J=2 Hz, ArH) and 7.96 (CH) ppm.

EXAMPLE 11

Employing the procedure of Example 10, and starting with the appropriate reagents, the following compounds were prepared:

| R₁ | R₅ | Y | m.p. °C. | NMR (CDCl₃) delta |
|---|---|---|---|---|
| C₂H₅ | (3,4-difluorophenyl) | O | 188–190 | 1.31 (J=7Hz, CH₃), 3.85 (J=7Hz, NCH₂), 4.4 (CH), 6.6–7.1 (ArH), 7.52 (J=2Hz, ArH), 8.0 (ArH), 8.22 (ArH) and 9.87 (NH). |
| C₂H₅ | (thiazol-2-yl) | O | 203–206 | 1.35 (J=7Hz, CH₃), 3.88 (J=7Hz, NCH₂), 4.53 (CH), 6.79 (ArH), 6.98 (J=4Hz, CH), 7.02 (ArH), 7.46 (J=4Hz, CH), 7.56 (J=2Hz, NH) and 7.98 (ArH). |
| C₂H₅ | (5-methylthiazol-2-yl) | S | 129–134 | HRMS (M/e) Calcd: 357.0605. Found: 357.0592. |

EXAMPLE 12

Again, employing the procedure of Example 10, and starting with the appropriate reagents, the following compounds were synthesized:

| $R_1$ | $R_5$ | Z | n | m.p. °C. | NMR (CDCl$_3$) delta |
|---|---|---|---|---|---|
| $C_2H_5$ | 2,4-difluorophenyl | O | 1 | 199–204 | (DMSO—d$_6$-NaOD) 1.08 J=7Hz, CH$_3$), 3.08 (CH$_2$), 4.37 (J=8Hz, CH$_2$), 6.3 (ArH), 6.6–7.3 (ArH), 7.49 (ArH) and 8.3–8.7 (ArH). |
| $C_2H_5$ | 4-fluorophenyl | O | 1 | 205–208 | 1.21 (J=7Hz, CH$_3$), 3.18 (J=8Hz, CH$_2$), 3.72 (J=7Hz, CH$_2$), 4.23 (CH), 4.57 (J=8Hz, CH$_2$O), 6.35 (ArH), 7.01 J=16 and 8Hz, ArH) and 7.4–7.7 (ArH). |
| $C_2H_5$ | phenyl | O | 1 | 187–188 | 1.28 (J=7Hz, CH$_3$), 3.2 (J=8Hz, CH$_2$), 3.75 (J=7Hz, NCH$_2$), 4.28 (CH), 4.6 (J=8Hz, CH$_2$O), 6.39 (ArH), 7.0–7.7 (ArH). |
| $C_2H_5$ | 2-pyridyl | O | 1 | 193–195 | (DMSO—d$_6$-NaOD) 1.05 (J=7Hz, CH$_3$), 3.02 (J=8Hz, CH$_2$), 4.32 (J=8Hz, CH$_2$O), 6.22 (ArH), 6.7 (ArH), 7.45 (ArH) and 8.05 (ArH). |
| $C_2H_5$ | 4-methylthiazo-2-yl | O | 1 | 216–219 | (DMSO—d$_6$- NaOD) 1.05 (J=7Hz, CH$_3$), 2.28 (J=1Hz, CH$_3$), 3.08 (J=8Hz, CH$_2$), 4.4 (J=8Hz, OCH$_2$), 6.38 (ArH), 6.89 (J=1Hz, CH) and 7.46 (ArH). |
| $C_2H_5$ | 2,4-difluorophenyl | CH$_2$ | 1 | 170–171 | 1.29 (J=7Hz, CH$_3$), 2.08 (CH$_2$), 2.91 (J=7Hz, CH$_2$), 3.83 (J=7Hz, NCH$_2$), 4.33 (CH), 6.7–7.1 (ArH), 7.58 (ArH), 8.22 (ArH) and 9.83 (NH). |
| $C_2H_5$ | thiazo-2-yl | CH$_2$ | 1 | 181–183 | 1.25 (J=7Hz, CH$_3$), 2.07 (CH$_2$), 2.90 (J=7Hz, CH$_2$), 3.79 (J=7Hz, NCH$_2$), 4.4 (NH), 6.75 (ArH), 6.94 (J=3Hz, CH), 7.43 (J=3Hz, CH), and 7.55 (ArH). |
| $C_2H_5$ | 4-methylthiazo-2-yl | CH$_2$ | 1 | 155–165 | 1.29 (J=7Hz, CH$_3$), 2.07 (CH$_2$), 2.40 (J=1Hz, CH$_3$), 2.94 (J=7Hz, CH$_2$), 3.79 (J=7Hz, NCH$_2$), 4.37 (CH), 6.76 (ArH), 7.02 (J=1Hz, CH) and 7.55 (ArH). |

EXAMPLE 13

N-(4-Fluorophenyl)-1-ethyl-2-oxo-2,3-dihydropyrano[2,3-f]indole-3-carboxamide (2, $R_1=C_2H_5$, $R_2=$4-fluorophenyl, $R_3$, $R_4=$H and n=2)

To a slurry of 128 mg. (3.2 mmoles) of sodium hydride (washed with petroleum ether) in 4 ml. of dimethylformamide was added 500 mg. (2.3 mmoles) of 1-ethyl-2-oxo-2,3-dihydro-pyrano[2,3-f]indole followed after 15 minutes of stirring by 0.36 ml. (3.2 mmoles) of 4-fluorophenylisocyanate. The reaction mixture was allowed to stir at room temperature for 30 minutes, and was then added to a mixture of dichloromethane (50 ml.) and ice water (50 ml.). The aqueous layer was extracted with 35 ml. of dichloromethane and was then acidified with 4N hydrochloric acid. The acidified layer was extracted with fresh dichloromethane, and the organic phase separated, dried over magnesium sulfate and concentrated under vacuum to dryness, 1.6 g. The residue was taken up in ethyl acetate, washed with a brine solution and dried over magnesium sulfate. Removal of the solvent gave 709 mg. of crude product. Recrystallization from dichloromethane-diisopropyl ether gave 490 mg. (60% yield) of product, m.p. 212°–214° C.

Anal. Calcd. for $C_{20}H_{19}O_3N_2F$: C, 67.8; H, 5.4; N, 7.9. Found: C, 67.3; H, 5.5; N, 8.2.

The NMR spectrum (CDCl$_3$) showed absorption at 1.3 (J=7 Hz, CH$_3$), 1.7–2.2 (CH$_2$), 2.8 (J=7 Hz, CH$_2$), 3.74 (J=7 Hz, NCH$_2$), 4.11 (J=5 Hz, CH$_2$), 4.25 (CH), 6.5 (ArH), 6.94 (J=8+8 Hz, ArH), 7.23 (ArH), 7.49 (J=8 Hz+6 Hz, ArH) and 9.73 (NH) ppm.

EXAMPLE 14

N-(4-Chlorophenyl)-1-ethyl-2-oxo-2,3,5,6-tetrahydro-7H-cyclopenta[f]indole-3-carboxamide (4, $R_1=C_2H_5$, $R_5=$4-chlorophenyl, Z=CH$_2$, n=1)

The procedure of Example 13 is employed starting with 3.0 g. (14.9 mmoles) of 1-ethyl-2-oxo-2,3,5,6-tetrahydro-7H-cyclopenta[f]indole and 2.59 g. (16.9 mmoles) of 4-chlorophenylisocyanate to give 650 mg. (12% yield) of the desired product, m.p. 191°–192.5° C.

Anal. Calcd. for $C_{20}H_{19}O_2N_2Cl$: C, 67.3; H, 5.4; N, 7.9. Found: C, 67.3; H, 5.4; N, 7.8.

EXAMPLE 15

N-(5-Methylthiazo-2-yl)-2-ethyl-3-oxo-3,4-dihydrofuro[3,2-g]indole-4-carboxamide (5, $R_1=C_2H_5$, $R_6=$5-methylthiazo-2-yl)

A reaction mixture comprised of 348 mg. (1.27 mmoles) of ethyl 2-ethyl-3-oxo-3,4-dihydro-furo[3,2-g]indole-4-carboxylate and 290 mg. (2.54 mmoles) of 2-amino-5-methylthiazole in 14 ml. of benzene was heated at reflux for 50 minutes with the reaction condenser fitted with a soxhlet filled with 4A molecular sieves. The reaction mixture was then added to 35 ml. of dichloromethane and 35 ml. of ice cold 1N hydrochloric acid. The organic layer was separated, dried over magnesium sulfate and concentrated in vacuo. The residual was recrystallized from dichloromethanediisopropyl ether, 365 mg. (84% yield), m.p. 165°–175° C. (dec.).

The NMR spectrum (CDCl$_3$) showed absorption at 1.3 (J=7 Hz, CH$_3$), 1.98 (CH$_3$), 4.1 (J=7 Hz, NCH$_2$), 6.7 (H), 6.72 (J=2 Hz, ArH), 7.16 (CH), 7.22 (J=8 Hz, ArH), 7.47 (J=2 Hz, ArH) and 7.72 (J=8 Hz, ArH) ppm.

EXAMPLE 16

Employing the procedure of Example 15, and starting with the appropriate reagents, the following 2-ethyl-3-oxo-3,4-dihydro-furo[3,2-g]indole-4-carboxamides are prepared:

![structure]

| $R_1$ | $R_6$ |
|---|---|
| $CH_3-$ | $4\text{-}FC_6H_4-$ |
| $C_2H_5-$ | $4\text{-}FC_6H_4-$ |
| $C_2H_5-$ | $3\text{-}FC_6H_4-$ |
| $C_2H_5-$ | $2\text{-}FC_6H_4-$ |
| $C_2H_5-$ | $2,4\text{-}F_2C_6H_3-$ |
| $C_2H_5-$ | $2,5\text{-}F_2C_6H_3-$ |
| $C_2H_3-$ | $3,5\text{-}F_2C_6H_3-$ |
| $CH_3-$ | 2-thiazolyl |
| $C_2H_5-$ | 2-pyridyl |
| $CH_3-$ | 4-pyridyl |
| $CH_3-$ | 5-methyl-2-thiazolyl |
| $n\text{-}C_3H_7$ | 2-pyridyl |

EXAMPLE 17

N-[2-(5-Methylthiazolyl)]-6,7-dihydro-5-ethyl-6-oxo-6H-furo[2,3-f]indole-7-carboxamide sodium salt To a suspension of 341 mg. (1.0 mmole) of N-[2-(5-methylthiazolyl)]-6,7-dihydro-5-ethyl-6-oxo-6H-furo[2,3-f]indole-7-carboxamide in 10 ml. of tetrahydrofuran was added 1 ml. of 1N sodium hydroxide solution. The resulting solution was reduced in volume in vacuo to give a semisolid which was suspended in water, cooled to 0° C. and filtered. The product was dried 1 hour at 110° C. (0.5 torr), 238 mg. (66% yield).

Anal. Calcd. for $C_{17}H_{14}N_3O_3NaS.\frac{1}{2}H_2O$: C, 54.8; H, 4.1; N, 11.3. Found: C, 54.8; H, 4.2; N, 11.2.

PREPARATION A

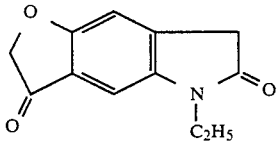

5-Ethyl-3,6-dioxo-2,3,6,7-tetrahydrofuro[2,3-f]indole

A1. 1-ethyl-5-chloroacetoxyoxindole

To a slurry of 100 g. (0.565 mole) of 1-ethyl-5-hydroxyoxindole in 91.3 ml. (1.13 moles) of pyridine and 565 ml. of dichloromethane at 0° C. was added dropwise a solution of 89.3 ml. (1.13 moles) of chloroacetyl chloride in 100 ml. of dichloromethane. The reaction mixture was allowed to stir for 15 minutes, and was then added to 1 l. of ice cold 2N hydrochloric acid and 500 ml. of dichloromethane. The aqueous layer was extracted once again with 300 ml. of dichloromethane and the combined organic extracts washed once with 500 ml. of a saturated brine solution, dried over magnesium sulfate and concentrated to give the desired product in quantitative yield. A small sample was crystallized from hexane, m.p. 53°–57° C.

The NMR spectrum (CDCl₃) showed absorption at 1.23 (J=7 Hz, CH₃), 3.5 (CH₂), 3.72 (J=7 Hz, NCH₂), 4.26 (ClCH₂) and 6.6–7.1 (ArH) ppm.

A2. 5-ethyl-3,6-dioxo-2,3,6,7-tetrahydrofuro[2,3-f]indole

To 142.9 g. (0.565 mole) of 1-ethyl-5-chloroacetoxyoxindole was added slowly 301 g. (2.26 moles) of aluminum chloride, and the resulting reaction mixture heated to 165° C. for one hour and then allowed to stir for 15 minutes. The hot reaction mixture was added to 4 l. of ice and water and the resulting precipitate filtered and dried. The aqueous filtrate was extracted (6×300 ml.) with dichloromethane, and the combined extracted dried over magnesium sulfate and concentrated to dryness. The residue was combined with filtered product and recrystallized from ethyl acetate, 85.9 g. (70%), m.p. 181°–184° C.

The NMR spectrum (CDCl₃) showed absorption at 1.29 (J=7 Hz, CH₃), 3.6 (CH₂), 3.78 (J=7 Hz, NCH₂), 4.66 (OCH₂), 6.99 (ArH) and 7.05 (ArH) ppm.

PREPARATION B

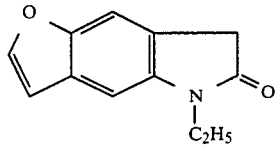

5-Ethyl-6-oxo-6,7-dihydro-furo[2,3-f]indole

B1. 5-ethyl-3-hydroxy-6-oxo-2,3,6,7-tetrahydrofuro[2,3-f]indole

To a slurry of 30 g. (0.138 mole) of 5-ethyl-3,6-dioxo-2,3,6,7-tetrahydrofuro[2,3-f]indole (Preparation A) in 1 l. of methanol cooled to 0° C. was added 5.24 g. (0.138 mole) of sodium borohydride. After 30 minutes an additional 2.6 g. (68.4 moles) of hydride was added and the reaction mixture allowed to stir for 1.5 hours. The reaction mixture was quenched by the addition of 50 ml. of a saturated brine solution and the resulting solution concentrated in vacuo. The residue was partitioned between 1 l. of a saturated brine solution and 1 l. of dichloromethane. The organic layer was separated and held, and the aqueous layer was extracted (4×300 ml.) with fresh dichloromethane. The organic extracts were combined, dried over magnesium sulfate and concentrated to give a quantitative yield of product. A small sample was recrystallized from diethyl ether, m.p. 144°–145° C.

The NMR spectrum (CDCl₃) showed absorption at 1.14 (J=7 Hz, CH₃), 3.45 (CH₂), 3.62 (J=7 Hz, NCH₂), 4.0–4.6 (OCH₂), 5.2 (CH), 5.5 (J=5 Hz, OH), 6.78 (ArH) and 6.92 (ArH) ppm.

B2. 5-ethyl-6-oxo-6,7-dihydro-furo[2,3-f]indole

To a slurry of 30.3 g. (0.138 mole) of 5-ethyl-3-hydroxy-6-oxo-2,3,6,7-tetrahydro-furo[2,3-f]indole in 950 ml. of acetonitrile at 25° C. was added 7 ml. of a 10% solution of trifluoroacetic acid in acetonitrile, and the reaction was allowed to stir at room temperature for 12 hours. The clear solution was evaporated to give a quantitative yield of the product. A small sample was recrystallized from hexane, m.p. 112°–113° C.

Anal. Calcd. for $C_{12}H_{11}O_2N$: C, 71.6; H, 5.5; N, 7.0. Found: C, 71.3; H, 5.5; N, 7.1.

PREPARATION C

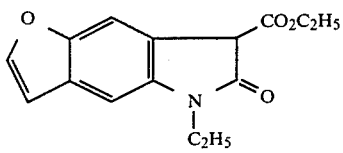

To a solution of 1.5M sodium ethoxide, formed by adding 9.52 g. (0.414 mole) of sodium metal to 276 ml. of dry ethanol, and cooled to 0° C. was added 50 ml. (0.414 mole) of diethylcarbonate followed by the addition of 27.7 g. (0.138 mole) of 5-ethyl-6-oxo-6,7-dihydro-furo[2,3-f]indole (Preparation B). The reaction mixture was heated at 65° C. for 2 hours and stirred at 25° C. for 15 hours. The reaction mixture was added to 1 l. of ice cold 1N hydrochloric acid-saturated brine solution (1:1, v:v) and 500 ml. of dichloromethane. The aqueous phase was further extracted with fresh dichloromethane (2×250 ml.) and the extracts combined dried over magnesium sulfate and concentrated under vacuum to give the crude product. Recrystallization from diethyl ether-hexane gave 30.9 g. (82% yield) of product, m.p. 74.5°–76.5° C.

The NMR spectrum (CDCl$_3$) showed absorption at 1.29 (J=7 Hz, CH$_3$), 3.81 (J=7 Hz, NCH$_2$), 4.21 (J=7 Hz, OCH$_3$), 4.5 (CH), 6.72 (ArH), 6.98 (ArH), 7.46 (ArH) and 7.56 (J=2 Hz, ArH) ppm.

PREPARATION D

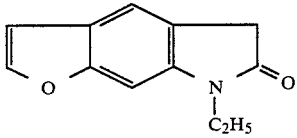

3-Ethyl-4-oxo-4,5-dihydro-furo[3,2-f]-indole

D1. 1-ethyl-6-chloroacetoxyoxindole

To a solution of 10 g. (56.5 mmoles) of 1-ethyl-6-hydroxyoxindole and 14.6 g. (120 mmoles) of 4-(N,N-dimethylamino)pyridine in 56 ml. of dichloromethane cooled to 0° C. was added 11.1 g. (65 mmoles) of chloroacetic anhydride. Additional portions of 4-(N,N-dimethylamino)pyridine (60 mmoles) and chloroacetic anhydride (30 mmoles) were added at 30, 60 and 90 minutes. After 2 hours, the reaction mixture was added to 500 ml. of ice cold 1N hydrochloric acid and 500 ml. of dichloromethane. The organic extract was washed once each with 300 ml. of 1N hydrochloric acid and 300 ml. of a saturated sodium bicarbonate solution. The organic phase was then dried over magnesium sulfate and evaporated to a semisolid which crystallized on the addition of diisopropyl ether-hexane, 9.11 g. (64% yield), m.p. 114°–116° C.

The NMR spectrum (CDCl$_3$) showed absorption at 1.22 (J=7 Hz, CH$_3$), 3.44 (CH$_2$), 3.7 (J=7 Hz, NCH$_2$), 4.28 (ClCH$_2$), 6.62 (ArH), 6.64 (J=8+2 Hz, ArH) and 7.16 (J=8 Hz, ArH) ppm.

D2. 3-ethyl-4,6-dioxo-4,5,6,7-tetrahydro-furofuro[3,2-f]indole

Using the procedure of Preparation A2, 9.0 g. (35.6 mmoles) of 1-ethyl-6-chloroacetoxyoxindole and 18.9 g. (0.142 mole) of aluminum chloride gave 6.2 g. (80% yield) of the title compound, m.p. 184°–186° C.

The NMR spectrum (CDCl$_3$) showed absorption at 1.26 (J=7 Hz, CH$_3$), 3.45 (J=1 Hz, CH$_2$), 3.73 (J=7 Hz, NCH$_2$), 4.58 (OCH$_2$), 6.42 (ArH) and 7.33 (ArH) ppm.

D3. 3-ethyl-4-oxo-6-hydroxy-4,5,6,7-tetrahydrofuro[3,2-f]indole

Following the procedure of Preparation 1B, 5.72 g. (26.4 mmoles) of 3-ethyl-4,6-dioxo-4,5,6,7-tetrahydrofuro[3,2-f]indole and 1.0 g. (26.4 mmoles) of sodium borohydride gave 5.2 g. (91% yield) of the desired product.

HRMS (M/e) Calcd. for $C_{12}H_{13}O_3N$: 219.0895 Found: 219.0888

D4. 3-ethyl-4-oxo-4,5-dihydro-furo[3,2-f]indole

Starting with 5.22 g. (23.8 mmoles) of 3-ethyl-4-oxo-6-hydroxy-4,5,6,7-tetrahydro-furo[3,2-f]indole and following the procedure of Preparation B2, 4.64 g. (97% yield) of the title compound was obtained.

The NMR spectrum (CDCl$_3$) showed absorption at 1.29 (J=7 Hz, CH$_3$), 3.6 (CH$_2$), 3.85 (J=7 Hz, NCH$_2$), 6.68 (J=2Hz, ArH), 6.93 (ArH), 7.38 (ArH) and 7.49 (J=2 Hz, ArH) ppm.

PREPARATION E

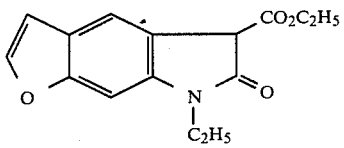

Ethyl 3-ethyl-4-oxo-4,5-dihydro-furo[3,2-f]indole-5-carboxylate

Using the procedure of Preparation C, and starting with 4.0 g. (19.9 mmoles) of 3-ethyl-4-oxo-4,5-dihydrofuro[3,2-f]indole, 1.36 g. (59.7 mmoles) of sodium metal and 7.23 ml. (59.7 mmoles) of diethylcarbonate, 3.25 g. (60% yield) of the desired product was obtained, m.p. 74°–77° C.

Anal. Calcd. for $C_{15}H_{15}O_4N$: C, 65.9; H, 5.5; N, 5.1. Found: C, 66.0; H, 5.5; N, 5.2

PREPARATION F

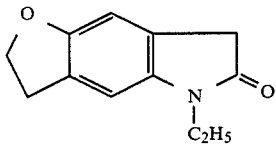

5-Ethyl-6-oxo-2,3,6,7-tetrahydro-furo[2,3-f]indole

F1. 5-ethylamino-2,3-dihydrobenzofuran

A mixture of 148 g. (1.09 moles) of 5-amino-2,3-dihydrobenzofuran and 93 g. of W2 Raney nickel in 850 ml. of ethanol was heated to reflux for 24 hours. The reaction was cooled to 25° C., filtered and evaporated to give a quantitative yield of the desired intermediate.

The NMR spectrum (CDCl$_3$) showed absorption at 1.2 (J=7 Hz, CH$_3$), 3.1 (NCH$_2$), 3.12 (J=7 Hz, CH$_2$), 3.26 (NH), 4.42 (J=7 Hz, OCH$_2$), 6.34 (J=8+2 Hz, ArH), 6.5 (ArH) and 6.62 (J=8 Hz, ArH) ppm.

F2. 5-ethyl-2,3-dihydro-furo[2,3-f]isatin

To a solution of 504 g. (4 moles) of oxalyl chloride in 350 ml. of dichloromethane cooled to 0° C. was added dropwise over 30 minutes a solution of 40.8 g. (0.25 mole) of 5-ethylamino-2,3-dihydrobenzofuran in 50 ml. of dichloromethane. The reaction was allowed to stir for 2 hours at 25° C. followed by evaporation of the solvent and excess oxalyl chloride in vacuo. The residue was dissolved in 575 ml. of dichloromethane and cooled to 0° C. To the cold solution was added 100 g. (0.752 mole) of aluminum chloride in several portions over a period of 5 minutes. The reaction mixture was stirred 5 minutes at 0° C. and then one hour at 25° C. It was then poured onto 2 l. of ice and water and extracted with dichloromethane. The extracts were dried over magnesium sulfate and evaporated to give the crude product, which was purified by chromatographing of 650 g. of silica gel, 22.1 g. (41% yield), m.p. 173°–174° C.

HRMS (M/e) Calcd. for C$_{12}$H$_{11}$O$_3$N: 217.0739. Found: 217.0731.

F3. 5-ethyl-2,3-dihydro-furo[2,3-f]isatin hydrazone

A mixture of 11.0 g. (50.7 mmoles) 5-ethyl-2,3-dihydro-furo[2,3-f]isatin and 1.86 g. (53.3 mmoles) of anhydrous hydrazine in 100 ml. of ethanol was heated to reflux for 30 minutes. The reaction was cooled to 0° C. and the product collected and dried, 10.4 g. (88% yield), m.p. 189°–190° C.

The NMR spectrum (d$_6$-DMSO) showed absorption at 1.12 and 1.16 (J=7 Hz, CH$_3$), 3.2 (J=8 Hz, CH$_2$), 3.6 and 3.62 (J=7 Hz, NCH$_2$), 4.51 (J=8 Hz, OCH$_2$), 6.77 and 7.49 (ArH), 6.98 (ArH) and 8.7 (NH$_2$) ppm.

F4. 5-ethyl-6-oxo-2,3,6,7-tetrahydro-furo[2,3-f]indole

To a solution of 3.6 g. (0.156 mole) of sodium metal in 117 ml. of ethanol was added 11.7 ml. of dimethylsulfoxide. The solution was heated to 55° C. and 9.0 g. (0.039 mole) of 5-ethyl-2,3-dihydro-furo[2,3-f]isatin hydrazone was added. The reaction was maintained at 70° C. for 3.5 hours followed by addition to an ice cold mixture of 500 ml. of a saturated brine solution and 94 ml. of 2N hydrochloric acid. The aqueous layer was extracted (4×100 ml.) with ethyl acetate and the combined extracts washed with a saturated sodium bicarbonate solution. The organic layer was dried over magnesium sulfate and evaporated. The product was purified by chromatographing on 150 g. of silica gel, 3.17 g. (40% yield), m.p. 106°–107° C.

HRMS (M/e) Calcd. for C$_{12}$H$_{13}$O$_2$N: 203.947. Found: 203.0939.

PREPARATION G

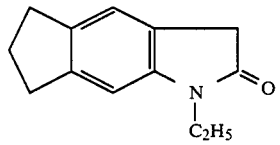

1-Ethyl-2oxo-2,3,5,6-tetrahydro-7H-cyclopenta[f]indole

G1. 2,3-dihydro-5-ethylamino-1H-indene

Using the procedure of Preparation F1, 47.0 g. (0.353 mole) of 5-amino-2,3-dihydro-1H-idene and 11 g. of W2 Raney nickel gave a quantitative yield of the title compound.

The NMR spectrum (CDCl$_3$) showed absorption at 1.21 (J=7 Hz, CH$_3$), 1.8–2.3 (CH$_2$), 2.8 (J=7 Hz, CH$_2$), 3.17 (J=7 Hz, NCH$_2$), 3.27 (NH), 6.4 (J=8+2 Hz, ArH), 6.5 (ArH) and 7.0 (J=8 Hz, ArH) ppm.

G2. 2,3-dihydro-5-(N-ethyl-N-bromoacetyl)amino-1H-indene

To a solution of 34.8 g. (0.172 mole) of bromoacetyl bromide in 155 ml. of benzene at 5° C. was added dropwise 55.5 g. (0.344 mole) of 2,3-dihydro-5-ethylamino-1H-indene in 15 ml. of benzene. The reaction was allowed to stir at 25° C. and an additional 3.7 g. (18.3 mmoles) of bromoacetyl bromide was added. The reaction was filtered and the filtrate diluted with ether and 500 ml. 0.5N hydrochloric acid. The organic extract was washed once with 1 l. of water and 1 l. of a saturated brine solution, dried over magnesium sulfate and concentrated to give 44.2 g. (91% yield) of the desired intermediate.

The NMR spectrum (CDCl$_3$) showed absorption at 1.11 (J=7 Hz, CH$_3$), 1.8–2.4 (CH$_2$), 2.91 (J=7 Hz, CH$_2$), 3.61 (BrCH$_2$), 3.77 (J=7 Hz, NCH$_2$), 6.9 (J=8+2 Hz, ArH), 7.0 (ArH) and 7.22 (ArH) ppm.

G3. 1-ethyl-2-oxo-2,3,5,6-tetrahydro-7H-cyclopenta[f]indole

To 44.2 g. (0.157 mole) of 2,3-dihydro-5-(N-ehtyl-N-bromoacetyl)amino-1H-indene at 25° C. was slowly added 26 g. (0.195 mole) of aluminum chloride. The reaction mixture was then heated to 180° C. over a 2 hour period. The hot reaction was quenched by addition to 350 ml. of ice-water. The quenched reaction mixture was extracted with diethyl ether-dichloromethane and the extracts washed with water, a saturated brine solution and dried over mangesium sulfate. Concentration of the extracts gave a crude product which was purified by chromatographing on 1 kg. of silica gel, 15.7 g. (50% yield), m.p. 90.5°–92° C.

The NMR spectrum (CDCl$_3$) showed absorption at 1.21 (J=7 Hz, CH$_3$), 2.02 (J=7 Hz, CH$_2$), 2.85 (J=7 Hz, CH$_2$), 3.36 (CH$_2$), 3.65 (J=7 Hz, NCH$_2$), 6.63 (ArH) and 7.0 (ArH) ppm.

PREPARATION H

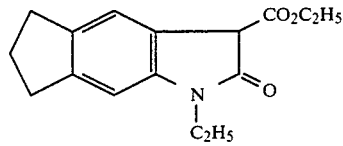

Ethyl 1-ethyl-2-oxo-2,3,5,6-tetrahydro-7H-cyclopenta[f]indole-3-carboxylate

Using the procedure of Preparation C, 5.00 g. (24.9 mmoles) of 1-ethyl-2-oxo-2,3,5,6-tetrahydro-7H-cyclopental[f]indole and 5.87 g. (49.7 mmoles) of diethylcarbonate gave 4.33 g. (64% yield) of the desired intermediate, m.p. 167.5° C.

HRMS (M/e) Calcd. for C$_{16}$H$_{18}$O$_3$N: 273.1365. Found: 273.1393

PREPARATION I

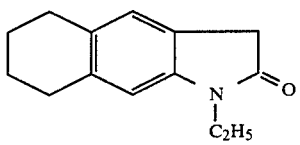

1-Ethyl-2-oxo-2,3-dihydro-cyclohexa[f]indole

I1. 6-ethylamino-1,2,3,4-tetrahydronaphthalene

Using the procedure of Preparation F1, 21.6 g. (0.146 mole) of a mixture of 5 and 6-amino-1,2,3,4-tetrahydronaphthalene and 36 g. of W2 Raney nickel gave 9.48 g. (37% yield) of the title intermediate after purification by column chromatography on 1 Kg. of silica gel using 10% diethyl ether-hexane as eluent.

The NMR spectrum (CDCl$_3$) showed absorption at 1.2 (J=7 Hz, CH$_3$), 1.75 (CH$_2$), 2.6 (CH$_2$), 3.08 (J=7 Hz, NCH$_2$), 3.2 (NH), 6.27 (ArH), 6.32 (J=8 Hz, ArH) and 6.76 (J=8 Hz, ArH) ppm.

I2. 6-(N-ethyl-N-bromoacetyl)amino-1,2,3,4-tetrahydronaphthalene

Following the procedure of Preparation G2, 9.48 g. (54 mmoles) of 6-ethylamino-1,2,3,4-tetrahydronaphthalene and 5.6 g. (27.7 mmoles) of bromoacetyl bromide gave 7.4 g. (92% yield) of the desired intermediate.

The NMR spectrum (CDCl$_3$) showed absorption at 1.11 (J=7 Hz, CH$_3$), 1.8 (CH$_2$), 2.76 (CH$_2$), 3.62 (BrCH$_2$), 3.7 (J=7 Hz, NCH$_2$), 6.82 (J=8 and 2 Hz, ArH), 6.86 (J=2 Hz, ArH) and 7.06 (J=8 Hz, ArH) ppm.

I3. 1-ethyl-2-oxo-2,3-dihydro-cyclohexa[f]indole

Using the procedure of Preparation G3 6.75 g. (22.8 mmoles) of 6-(N-ethyl-N-bromoacetyl)amino-1,2,3,4-tetrahydronaphthalene and 3.78 g. (28.3 mmoles) of aluminum chloride gave 346 mg. (7% yield) of the desired product and 1.38 g. (28% yield) of 1-ethyl-2-oxo-2,3-dihydro-cyclohexa[e]indole as separated by fractional crystallization from methanol and preparative reverse phase high pressure liquid chromatography (C-18, 65% aqueous acetonitrile), m.p. 124°–125.5° C.

The NMR spectrum (CDCl$_3$) showed absorption at 1.22 (J=7 Hz, CH$_3$), 1.83 (CH$_2$), 2.8 (CH$_2$), 3.48 (CH$_2$), 3.78 (J=7 Hz, NCH$_2$), 6.5 (ArH) and 6.9 (ArH) ppm.

PREPARATION J

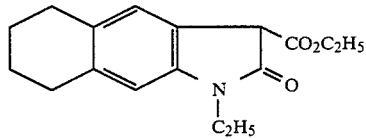

Ethyl 1-ethyl-2-oxo-2,3-dihydro-cyclohexa[f]indole-3-carboxylate

Employing the procedure of Preparation C, 296 mg. (1.38 mmoles) of 1-ethyl-2-oxo-2,3-dihydro-cyclohexa[f]indole and 325 mg (2.75 mmoles) of diethylcarbonate gave a quantitative yield of the title compound as an oil.

The NMR spectrum (CDCl$_3$) showed absorption at 1.25 (J=7 Hz, CH$_3$),1.78 (CH$_2$), 2.72 (CH$_2$), 3.71 (J=7 Hz, NCH$_2$), 4.2 (J=7 Hz, OCH$_2$), 4.27 (CH), 6.5 (ArH) and 7.0 (ArH) ppm.

PREPARATION K

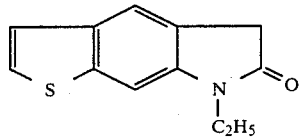

3-ethyl-4-oxo-4,5-dihydro-thieno[3,2-f]inole

K1. 6-(p-tolylsulfonylamino)benzothiphene

A mixture of 8.85 g. (59.4 mmoles) of 6-aminobenzothiophene and 12.1 g. (63.6 mmoles) of p-tolylsulfonyl chloride in 90 ml. of pyridine was stirred at 25° C. for 4 hours. The reaction mixture was then added to 1.5 l. of cold water, and the resultant mixture extracted with diethyl ether (3×200 ml.). The combined extracts were washed with 0.5N hydrochloric acid (4×250 ml.), 250 ml. of a saturated brine solution and dried over magnesium sulfate. Removal of the solvent gave 17.3 g. (96% yield) of the desired product, m.p. 141°–143° C.

Anal. Calcd. for $C_{15}H_{13}O_2NS_2$: C, 59.4; H, 4.3; N, 4.6. Found: C, 59.5; H, 4.4; N, 4.6.

K2. 6-(N-ethyl-N-p-tolylsulfonylamino)benzothiophene

To a slurry of 1.58 g. (65.8 mmoles) of sodium hydride in 114 ml. of dimethylformamide was added gradually 17.3 g. (57.1 mmoles) of 6-(p-tolylsulfonylamino)-benzothiophene. The reaction mixture was stirred 20 minutes and 10.1 g (65.7 mmoles) of diethyl sulfate was added. The stirring was continued for 16 hours at 25° C. and the reaction mixture added to 1 l. of a saturated brine solution. The mixture was then extracted (4×400 ml.) with diethyl ether. The extracts were combined, washed with water (2×1 l.) once with a saturated brine solution (1 l.) and dried over magnesium sulfate. Removal of the solvent gave 16.6 g. (88% yield) of the desired product, m.p. 134°–136° C.

The NMR spectrum (CDCl$_3$) showed absorption at 1.06 (J=7 Hz, CH$_3$), 2.4 (CH$_3$), 3.61 (J=7 Hz, CH$_2$) and 6.85-7.8 (ArH) ppm.

K3. 6-ethylaminobenzothiophene

A mixture of 15.4 g. (46.6 mmoles) of 6-(N-ethyl-N-p-tolylsulfonylamino)benzothiophene, 77 ml. of acetic acid, 23 ml. of concentrated sulfuric acid and 15.4 ml. of water was heated at reflux for 1.75 hours. The cooled reaction was added to 750 ml. of water and the mixture extracted with (3×300 ml.) diethyl ether. The aqueous phase was cooled in ice and made basic by the addition of 0.5 l. of 5N sodium hydroxide solution. The mixture was extracted with (3×300 ml.) diethyl ether and the combined extracts dried over magnesium sulfate and concentrated to dryness, 6.8 g. (82% yield).

HRMS (M/e) Calcd. for $C_{10}H_{11}NS$: 177.0609. Found: 177.0603.

K4. 3-ethyl-thieno[3,2-f]isatin

Using the procedure of Preparation F2, 5.71 g. (32.3 mmoles) of 6-ethylaminobenzothiophene, 56.1 g. (0.651 mole) of oxalyl chloride and 8.56 g. (64.4 mmoles) of aluminum chloride gave 8.26 g. of crude product, which was purified by column chromatography on 1 Kg. of silica gel using 75–100% dichloromethane-hexane as eluent. There was obtained, in order of elution 1.62 g. (22% yield) of 1-ethyl-thieno[2,3-d]isatin and 2.18 g. (29% yield) of the titled compound, m.p. 200°-202° C.

Anal. Calcd. for $C_{12}H_9O_2NS$: C, 62.3; H, 3.9; N, 6.1. Found: C, 62.4; H, 4.2; N, 5.9.

K5. 3-ethyl-3-oxo-3,4-dihydro-5,5-dichloro-thieno[3,2-f]indole

A mixture of 1.33 g. (5.76 mmoles) of 3-ethyl-thieno[3,2-f]isatin and 1.8 g. (7.55 mmoles) of phosphorus pentachloride in 5.7 ml. of benzene was heated at reflux for 45 minutes. The reaction was cooled to 25° C. and filtered through 24 g. of neutral alumina. Evaporation of the eluent gave 1.38 g. (84% yield) of the desired intermediate.

The NMR spectrum ($CDCl_3$) showed absorption at 1.33 (J=7 Hz, $CH_3$), 3.86 (J=7 Hz, $NCH_2$), 7.1-7.5 (ArH) and 8.0 (ArH) ppm.

K6. 3-ethyl-4-oxo-4,5-dihydro-thieno[3,2-f]indole

To a slurry of 1.78 g. (6.22 mmoles) of 3-ethyl-3-oxo-3,4-dihydro-5,5-dichloro-thieno[3,2-f]indole in 30 ml. of glacial acetic acid was added 2.01 g. (30.9 mmoles) of zinc dust. The reaction mixture was stirred 30 minutes and then added 1 l. of ice water. The mixture was extracted (4×100 ml.) with diethyl ether and the combined extracts washed with a saturated sodium bicarbonate and a saturated brine solution. After drying over magnesium sulfate the extract was evaporated to give a residue which was purified by chromatographing on 50 g. of silica gel using dichloromethane as the eluent, 935 mg. (69% yield), m.p. 121.5°-126° C.

The NMR spectrum ($CDCl_3$) showed absorption at 1.28 (J=7 Hz, $CH_3$), 3.52 (J=1 Hz, $CH_2$), 3.84 (J=7 Hz, $NCH_2$), 7.2 (ArH) and 7.59 (ArH) ppm.

PREPARATION L

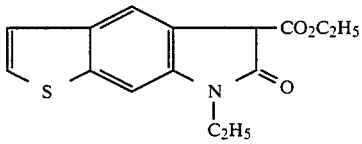

Ethyl 3-ethyl-4-oxo-4,5-dihydro-thieno[3,2-f]indole-5-carboxylate

Using the procedure of Preparation C, 900 mg. (4.15 mmoles) of 3-ethyl-4-oxo-4,5-dihydro-thieno[3,2-f]indole and 1.5 ml. (12.5 mmoles) of diethyl carbonate gave 829 mg. (69% yield) of the desired intermediate.

The NMR spectrum ($CDCl_3$) showed absorption at 1.21 and 1.24 (J=7 Hz, $CH_3$), 3.79 (J=7 Hz, $NCH_2$), 4.2 (J=7 Hz, $OCH_2$), 4.41 (J=1 Hz, CH), 7.25 (ArH) and 7.65 (J=1 Hz, ArH) ppm.

PREPARATION M

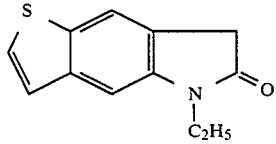

5-Ethyl-6-oxo-6,7-dihydro-thieno[2,3-f]indole

M1. 5-(p-tolylsulfonylamino)benzothiophene

Employing the procedure of Preparation K1, 45.5 g. (0.305 mole) of 5-aminobenzothiophene and 63.2 g. (0.327 mole) of p-toluenesulfonyl chloride gave 84.8 g. (92% yield) of the titled compound, m.p. 126°-136° C.

HRMS (M/e) Calcd. for $C_{15}H_{13}O_2N_2S_2$: 303.0387. Found: 303.0378.

M2. 5-(N-ethyl-N-p-tolylsulfonylamino)benzothiophene

Using the procedure of Preparation K2, 84.8 g. (0.28 mole) of 5-(p-tolylsulfonylamino)benzothiophene and 42 ml. (0.32 mole) of diethylsulfate gave 67.6 g. (73% yield) of the desired intermediate, m.p. 119°-121° C.

The NMR spectrum ($CDCl_3$) showed absorption at 1.07 (J=7 Hz, $CH_3$), 2.41 ($CH_3$), 3.66 (J=7 Hz, $NCH_2$) and 6.8-7.9 (ArH) ppm.

M3. 5-ethylaminobenzothiophene

Using the procedure of Preparation K3, 67.6 g. (0.204 mole) of 5-(N-ethyl-N-p-tolylsulfonylamino)benzothiophene gave 36.1 g. (100% yield) of the titled compound as an oil.

The NMR spectrum ($CDCl_3$) showed absorption at 1.2 (J=7 Hz, $CH_3$), 3.19 (J=7 Hz, $CH_2$), 3.4 (NH), 6.62 (J=8+2 Hz, ArH), 6.92 (J=2 Hz, ArH), 7.09 (J=6 Hz, ArH), 7.3 (J=6 Hz, ArH) and 7.58 (J=8 Hz, ArH) ppm.

M4. 5-Ethyl-thieno[2,3-f]isatin

Employing the procedure of Preparation K4, 33.8 g. (0.19 mole) of 5-ethylaminobenzothiophene and 332 ml. (3.8 moles) of oxalyl chloride gave 44.3 g. of crude product. The product was purified by chromatographing on 1 Kg. of silica gel using 25% hexanedichloromethane as the eluent. There was obtained, in order of elution, 13 g. (29% yield) of 4-ethyl-thieno[3,2-e]isatin and 3.8 g. (9% yield) of the titled compound, m.p. 144°-148° C.

Anal. Calcd. for $C_{12}H_9O_2NS$: C, 62.3; H, 3.9; N, 6.1. Found: C, 62.1; H, 4.1; N, 5.9.

M5. 5-ethyl-6-oxo-6,7-dihydro-7,7-dichloro-thieno[2,3-f]indole

Employing the procedure of Preparation K5, 4.51 g. of 5-ethyl-thieno[2,3-f]isatin and 6.09 g. (25.6 mmoles) of phosphorous pentachloride gave 3.69 g. (66% yield) of the desired intermediates.

The NMR spectrum ($CDCl_3$) showed absorption at 1.35 (J=7 Hz, $CH_3$), 3.83 (J=7 Hz, $NCH_2$), 7.2 (ArH), 7.28 (J=6 Hz, ArH), 7.62 (J=6 Hz, ArH) and 8.09 (ArH) ppm.

M6. 5-ethyl-6-oxo-6,7-dihydro-thieno[2,3-f]indole

Using the procedure of Preparation K6, 3.69 g. (12.9 mmoles) of 5-ethyl-6-oxo-6,7-dihydro-7,7-dichloro-thieno[2,3-f]indole and 4.17 g. (64.2 mmoles) of zinc dust gave 1.8 g. (64% yield) of the titled compound, m.p. 143°-144° C.

HRMS (M/e) Calcd. for $C_{11}H_{11}ONS$: 218.0595. Found: 218.0587.

PREPARATION N

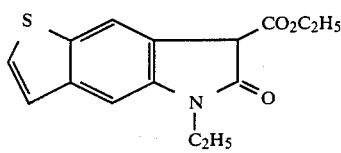

Ethyl 5-ethyl-6-oxo-6,7-dihydro-thieno[2,3-f]indole

Employing the procedure of Preparation C, 1.76 g. (8.11 mmoles) of 5-ethyl-6-oxo-6,7-dihydro-thieno[2,3-f]indole and 2.87 g. (24.3 mmoles) of diethyl carbonate gave 2.1 g. (90% yield) of the desired product as an oil.

The NMR spectrum (CDCl$_3$) showed absorption at 1.27 and 1.31 (J=7 Hz, CH$_3$), 3.88 (J=7 Hz, NCH$_2$), 4.27 (J=7 Hz, OCH$_2$), 4.25 (CH), 7.18 (ArH), 7.23 (J=5 Hz, ArH), 7.42 (J=5 Hz, ArH) and 7.75 (ArH) ppm.

PREPARATION O

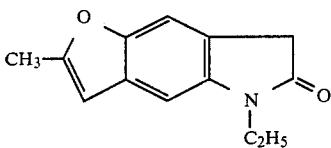

2-Methyl-5-ethyl-6-oxo-6,7-dihydro-furo[2,3-f]indole

O1. 1-ethyl-5-(alpha-chloropropionyloxy)oxindole

Using the procedure of Preparation A1, 5.0 g. (28.3 mmoles) of 1-ethyl-5-hydroxyoxindole and 7.17 (56.5 mmoles) of alpha-chloropropionyl chloride gave a quantitative yield of the title intermediate.

The NMR spectrum (CDCl$_3$) showed absorption at 1.24 (J=7 Hz, CH$_3$), 1.83 (J=7 Hz, CH$_3$), 3.51 (CH$_2$), 3.75 (J=7 Hz, NCH$_2$), 4.59 (J=7 Hz, CHCl) and 6.6–7.1 (ArH) ppm.

O2. 2-methyl-5-ethyl-3,6-dioxo-2,3,6,7-tetrahydrofuro[2,3-f]indole

Employing the procedure of Preparation A2, 7.54 (28.3 mmoles) of 1-ethyl-5-(alpha-chloropriopionyloxy)oxindole and 11.3 g. (84.8 mmoles) of aluminum chloride gave 1.39 (21% yield) of the desired intermediate, m.p. 149°–152° C.

The NMR spectrum (CDCl$_3$) showed absorption at 1.23 (J=7 Hz, CH$_3$), 1.52 (J=7 Hz, CH$_3$), 3.59 (CH$_2$), 3.74 (J=7 Hz, NCH$_2$), 4.61 (J=7 Hz, CH), 6.94 (ArH) and 7.02 (ArH) ppm.

O3. 2-methyl-5-ethyl-3-hydroxy-6-oxo-2,3,6,7-tetrahydro-furo[2,3-f]indole

Employing the procedure of Preparation B1, 2.01 g. (8.7 mmoles) of 2-methyl-5-ethyl-3,6-dioxo-2,3,6,7-tetrahydro-furo[2,3-f]indole and 330 mg. (8.7 mmoles) of sodium borohydride gave a quantitative yield of the desired compound, m.p. 123°–135° C.

The NMR spectrum (CDCl$_3$) showed absorption at 1.22 (J=7 Hz, CH$_3$), 1.38 and 1.51 (J=6.5 Hz, CH$_3$), 3.4 (CH$_2$), 3.68 (J=7 Hz, NCH$_2$), 4.57 (CH), 4.9 (CH), 6.7 (ArH) and 6.79 and 6.8 1 (ArH) ppm.

O4. 2-methyl-5-ethyl-6-oxo-6,7-dihydro-furo[2,3-f]indole

Using the procedure of Preparation B2, 2.03 g. (8.7 mmoles) of 2-methyl-5-ethyl-3-hydroxy-6-oxo-2,3,6,7-tetrahydro-furo[2,3-f]indole gave 1.51 g. (81% yield) of the desired compound, m.p. 109°–110° C.

Anal. Calcd. for C$_{13}$H$_{13}$O$_2$N: C, 72.5; H, 6.1; N, 6.5. Found: C, 72.4; H, 6.1; N, 6.5.

PREPARATION P

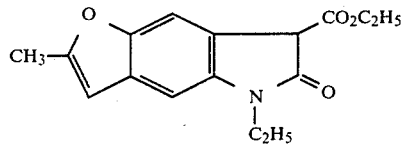

Ethyl 2-methyl-5-ethyl-6-oxo-6,7-dihydrofuro[2,3-f]indole-7-carboxylate

Starting with 1.5 g. (6.98 mmoles) of 2-methyl-5-ethyl-6-oxo-6,7-dihydro-furo[2,3-f]indole and 2.47 g. (20.9 mmoles) of diethyl carbonate, and following the procedure of Preparation C, 1.7 g. (85% yield) of the desired intermediate was obtained, m.p. 82°–90° C.

Anal. Calcd. for C$_{16}$H$_{17}$O$_4$N: C, 66.9; H, 6.0; N, 4.9. Found: C, 67.2; H, 6.2; N, 4.9.

PREPARATION Q

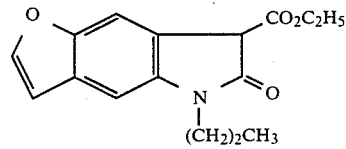

Ethyl 5-n-propyl-6-oxo-6,7-dihydro-furo[2,3-f]indole-7-carboxylate

Q1. p-(N-n-propyl-N-chloroacetyl)anisidine

Following the procedure of Preparation G2, 56.3 g. (0.341 mole) of p-N-n-propylanisidine and 38.5 g. (0.341 mole) of chloroacetyl chloride gave 79.8 g. (97% yield) of the titled compound, which was used without further purification.

Q2. 1-n-propyl-5-hydroxyoxindole

Employing the procedure of Preparation G3 79.8 g. (0.33 mole) of p-(N-n-propyl-N-chloroacetyl)anisidine and 132 g. (0.991 mole) of aluminum chloride gave 38.9 g. (62% yield) of the desired compound.

The NMR (CDCl$_3$) showed absorption at 0.92 (t, J=7 Hz, CH$_3$), 1.68 (sextet, J=7 Hz, CH$_2$), 3.45 (s, CH$_2$), 3.63 (t, J=7 Hz, NCH$_2$), 6.5–7.0 (m, 3ArH) and 7.47 (b, OH) ppm.

Q3. 1-n-propyl-5-chloroacetoxyoxindole

Employing the procedure of Preparation A1, 37.9 g. (0.198 mole) of 1-n-propyl-5-hydroxyoxindole and 31.3 ml. (0.396 mole) of chloroacetyl chloride gave a quantitative yield of the desired intermediate.

Q4. 5-n-propyl-3,6-dioxo-2,3,6,7-tetrahydrofuro[2,3-f]indole

Using the procedure of Preparation A2, 53 g. (0.198 mole) of 1-n-propyl-5-chloroacetoxyoxindole and 106 g. (0.972 mole) of aluminum chloride gave a quantitative yield of the desired intermediate.

The NMR (CDCl$_3$) showed absorption at 0.93 (t, J=7 Hz, CH$_3$), 1.65 (sextet, J=7 Hz, CH$_2$), 3.57 (s, CH₂), 3.63 (t, J=7 Hz, NCH₂), 4.61 (s, OCH₂), 6.92 (s, ArH) and 7.02 (bs, ArH) ppm.

Q5. 5-n-propyl-3-hydroxy-6-oxo-2,3,6,7-tetrahydrofuro[2,3-f]indole

Employing the procedure of Preparation A3 6.50 g. (28.1 mmoles) of 5-n-propyl-3,6-dioxo-2,3,6,7-tetrahydrofuro[2,3-f]indole and 1.06 g. (28.1 mmoles) of sodium borohydride gave 6.45 g. (98% yield) of the titled compound.

The NMR (CDCl₃)-DMSO-d₆) showed absorption at 0.96 (t, J=7 Hz, CH₃), 1.65 (sextet, J=7 Hz, CH₂), 3.41 (s, CH₂),3.59 (t, J=7 Hz, NCH₂), 4.45 (m, OCH₂, OH), 5.35 (m, CH), 6.72 (bs, ArH) and 6.85 (s, ArH) ppm.

Q6. 5-n-propyl-6-oxo-6,7-dihydro-furo[2,3-f]indole

Using the procedure of Preparation B2, 6.35 g. (27.3 mmoles) of 5-n-propyl-3-hydroxy-6-oxo-2,3,6,7-tetrahydro-furo[2,3-f]indole gave 5.0 g. (85% yield) of the titled intermediate, m.p. 90°–92° C.

The NMR (CDCl₃) spectrum showed absorption at 0.98 (t, J=7 Hz, CH₃), 1.73 (sextet, J=7 Hz, CH₂), 3.59 (s, CH₂), 3.69 (t, J=7 Hz, NCH₂), 6.65 (bs, ArH), 6.89 (bs, ArH), 7.3 (bs, ArH) and 7.52 (bs, ArH) ppm.

Anal. Calcd. for C₁₃H₁₃NO₂: C, 72.5; H, 6.1; N, 6.5. Found: C, 72.3; H, 6.4; N, 6.4.

Q7. ethyl 5-n-propyl-6-oxo-6,7-dihydro-furo[2,3-f]indole-7-carboxylate

Using the procedure of Preparation C, 3.0 g. (14.0 mmoles) of 5-n-propyl-6-oxo-6,7-dihydro-furo[2,3-f]indole and 4.94 g. (41.9 mmoles) of diethyl carbonate gave 2.5 g. (63% yield) of the titled compound.

The NMR (CDCl₃) spectrum showed absorption at 0.95 (t, J=7 Hz, CH₃), 1.22 (t, J=7 Hz, CH₃), 1.7 (sextet, J=7 Hz, CH₂), 3.7 (t, J=7 Hz, NCH₂), 4.2 (q, J=7 Hz, OCH₂), 4.42 (s, CH), 6.7 (bs, ArH), 6.93 (s, ArH), 7.42 (s, ArH) and 7.56 (d, J=2 Hz, ArH) ppm.

PREPARATION R

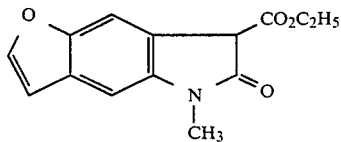

Ethyl 5-methyl-6-oxo-6,7-dihydro-furo[2,3-f]indole-7-carboxylate

R1. 1-methyl-5-chloroacetoxyoxindole

Employing the procedure of Preparation D1, 11.1 g. (68.0 mmoles) of 1-methyl-5-hydroxyoxindole and 17.4 g. (102 mmoles) of chloroacetic anhydride gave 4.58 g. (28% yield) of the titled intermediate, m.p. 93°–96° C.

The NMR (CDCl₃) spectrum showed absorption at 3.2 (s, NCH₃), 3.5 (s, CH₂), 4.29 (s, CH₂Cl) and 6.6–7.1 (m, ArH) ppm.

R2. 5-methyl-3,6-dioxo-2,3,6,7-tetrahydro-furo[2,3-f]indole

Using the procedure of Preparation A2, 4.5 g. (18.8 mmoles) of 1-methyl-5-chloroacetoxyoxindole and 10 g. (75.3 mmoles) of aluminum chloride gave 1.52 g. (40% yield) of the desired intermediate.

The NMR (DMSO-d₆) spectrum showed absorption at 3.13 (s, NCH₃), 3.65 (s, CH₂), 4.76 (s, OCH₂), 7.02 (s, ArH) and 7.20 (s, ArH) ppm.

R3. 5-methyl-3-hydroxy-6-oxo-2,3,6,7-tetrahydrofuro[2,3-f]indole

Following the procedure of Preparation A3, 1.45 (7.14 mmoles) of 5-methyl-3,6-dioxo-2,3,6,7-tetrahydrofuro[2,3-f]indole and 271 mg. (7.14 mmoles) of sodium borohydride gave 1.23 g. (84% yield) of the titled compound.

HRMS (M/e) Calcd. for C₁₁H₁₁NO₃: 205.0739. Found: 205.0758.

R4. 5-methyl-6-oxo-6,7-dihydro-furo[2,3-f]indole

Using the procedure of Preparation B2, 1.21 g. (5.9 mmoles) of 5-methyl-3-hydroxy-6-oxo-2,3,6,7-tetrahydro-furo[2,3-f]indole gave a quantitative yield of the desired compound.

The NMR (CDCl₃) spectrum showed absorption at 3.03 (s, CH₃), 3.72 (bs, CH₂), 6.71 (m, ArH), 6.98 (s, ArH), 7.37(s, ArH) and 7.61 (d, J=2 Hz, ArH) ppm.

R5. ethyl 5-methyl-6-oxo-6,7-dihydro-furo[2,3-f]indole-7-carboxylate

Following the procedure of Preparation C, 1.06 g. (5.67 mmoles) of 5-methyl-6-oxo-6,7-dihydro-furo[2,3-f]indole and 2.01 g. (17.0 mmoles) of diethyl carbonate gave 1.21 g. (82% yield) of the titled intermediate, m.p. 124°–126° C.

HRMS (M/e) Calcd. for C₁₄H₁₃NO₄: 259.0844. Found: 259.0847.

PREPARATION S

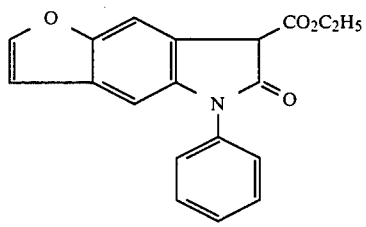

Ethyl 5-phenyl-6-oxo-6,7-dihydro-furo[2,3-f]indole-7-carboxylate

S1. 1-phenyl-5-methoxyindole

A mixture of 50 g. (0.34 mole) of 5-methoxyindole, 78 g. (0.497 mole) of bromobenzene, 49.7 g. (0.36 mole) of potassium carbonate and 9.76 g. (0.034 mole) of cuprous bromide in 330 ml. of N-methyl-2-pyrrolidone was heated to 190° C. for 24 hours. An additional 9.76 g. of cuprous bromide and 49.7 g. of potassium carbonate were added and heating at 190° C. continued for an additional 48 hours. The reaction was cooled to 25° C. and added to 1.5 l. of ice and water and 500 ml. of ethyl acetate. The quenched reaction mixture was filtered through celite with ethyl acetate. The organic layer was separated, washed with water (2×800 ml.) and once with 800 ml. of a saturated brine solution. The organic phase was dried over magnesium sulfate and concentrated to a crude oil, which was purified by distillation to give 58 g. (75% yield), b.p. 148° C. (0.3 torr).

Anal. Calcd. for C₁₅H₁₃NO: C, 80.7; H, 5.9; N, 6.3. Found: C, 80.5; H, 5.8; N, 6.6.

S2. 1-phenyl-5-methoxyoxindole

To a solution of 56.1 g. (0.248 mole) of 5-methoxy-1-phenyl-indole in 720 ml. dichloromethane was added 33.1 g. (0.248 mole) of N-chlorosuccinimide. The reaction was stirred 1 hour at 25° C. and then concentrated in vacuo. The residue was dissolved in 500 ml. glacial acetic acid, the solution heated to 80° C. and 252 ml. of 85% phosphoric acid added. The resultant mixture was heated at reflux for 1.5 hours and then cooled and stirred 16 hours at 25° C. The reaction mixture was then poured into a mixture of 1.5 kg. potassium carbonate and 6 l. ice-water. The quenched reaction was extracted with three 500 ml. portions of ethyl acetate. The combined organic extract was washed twice with 500 ml. saturated potassium carbonate, once with 500 ml. saturated sodium chloride, dried over magnesium sulfate and evaporated to an oil. Crystallization of this crude oil from ether-dichloromethane gave 24.4 g. (40%) of the title compound, m.p. 108°–110° C.

The NMR (CDCl$_3$) spectrum showed absorption at 3.63 (s, CH$_2$), 3.76 (s, OCH$_3$), 6.63 (m, ArH), 6.82 (m, ArH) and 7.37 (bs, ArH) ppm.

S3. 1-phenyl-5-hydroxyoxindole

A mixture of 22.2 g. (92.7 mmoles) of 1-phenyl-5-methoxyoxindole and 37.0 g. (0.278 mole) of aluminum chloride was gradually heated to 230° C. over a period of 1.5 hours. The solid reaction was cooled to 25° C. and the flask broken into 2 l. of ice-water. The mixture was allowed to stir for 16 hours and was then filtered. The solids were dissolved in ethyl acetate, dried over magnesium sulfate and crystallized by the addition of hexane, 12.5 g. (60% yield), m.p. 208°–211° C.

Anal. Calcd. for C$_{14}$H$_{11}$NO$_2$: C, 74.7; H, 4.9; N, 6.2. Found: C, 74.3; H, 5.3; N, 6.1.

S4. 1-phenyl-5-chloroacetoxyoxindole

Using the procedure of Preparation A1, 12.4 g. (54.9 mmoles) of 1-phenyl-5-hydroxyoxindole and 12.4 g. (0.11 mole) of chloroacetyl chloride gave a quantitative yield of the desired intermediate.

The NMR (CDCl$_3$) spectrum showed absorption at 3.71 (s, CH$_2$), 4.27 (s, CHCl), 6.76 (d, J=8 Hz, ArH), 6.92 (d, J=2 Hz, ArH) and 7.0–7.6 (m, ArH) ppm.

S5. 5-phenyl-3,6-dioxo-2,3,6,7-tetrahydro-furo[2,3-f]indole

Employing the procedure of Preparation A2, 16.6 g. (54.9 mmoles) of 1-phenyl-5-chloroacetoxyoxindole and 29.3 g. (220 mmoles) of aluminum chloride gave 3.34 g. (23% yield) of the titled intermediate, m.p. 232° C.

The NMR (CDCl$_3$) spectrum showed absorption at 3.76 (s, CH$_2$), 4.52 (s, CH$_2$O), 6.84 (s, ArH), 7.02 (s, ArH) and 7.33 (m, ArH) ppm.

S6. 5-phenyl-3-hydroxy-6-oxo-2,3,6,7-tetrahydrofuro[2,3-f]indole

Following the procedure of Preparation A3, 3.27 g. (12.3 mmoles) of 5-phenyl-3,6-dioxo-2,3,6,7-tetrahydro-furo[2,3-f]indole and 467 mg. (12.3 mmoles) of sodium borohydride gave a quantitative of the desired compound.

The NMR (CDCl$_3$+DMSO-d$_6$) spectrum showed absorption at 3.63 (s, CH$_2$), 4.15–4.65 (m, CH$_2$O), 5.22 (m, CH), 6.81 (s, ArH) and 7.42 (bs, ArH) ppm.

S7. 5-phenyl-6-oxo-6,7-dihydro-furo[2,3-f]indole

Following the procedure of Preparation B2, 3.2 g. (12.0 mmoles) of 5-phenyl-3-hydroxy-6-oxo-2,3,6,7-tetrahydro-furo[2,3-f]indole gave 2.5 g. (84% yield) of the desired intermediate, m.p. 135°–140° C.

The NMR (CDCl$_3$) spectrum showed absorption at 3.75 (s, CH$_2$), 6.6 (d, J=2 Hz, ArH), 6.85 (s, ArH), 7.45 (bs, ArH) and 7.52 (d, J=2 Hz, ArH) ppm.

S8. ethyl 5-phenyl-6-oxo-6,7-dihydro-furo[2,3-f]indole-7-carboxylate

Using the procedure of Preparation C, 2.0 g. (8.03 mmoles) of 5-phenyl-6-oxo-6,7-dihydro-furo[2,3-f]in-dole and 2.84 g. (24.1 mmoles) of diethyl carbonate gave a crude product. The crude product was dissolved in diethyl ether and the solids removed by filtration. The filtrate was diluted to 50 ml. with diethyl ether and subsequently washed with 50 ml. of 1N sodium hydroxide solution. The ether phase was separated, dried over magnesium sulfate and concentrated in volume. The precipitated sodium salt of the desired compound, 580 mg., was filtered, added to 50 ml. of ether and 50 ml. of 1N hydrochloric acid. The ether layer was separated, dried and evaporated to give 490 mg. (19% yield) of the desired intermediate as an oil.

The NMR (CDCl$_3$+DMSO-d$_6$) spectrum of the sodium salt showed absorption at 1.29 (t, J=7 Hz, CH$_3$), 4.24 (q, J=7 Hz, CH$_2$), 6.6 (d, J=2 Hz, ArH), 7.0 (s, ArH), 7.25 (s, ArH), 7.5 (d, J=2 Hz, ArH) and 7.71 (s, ArH) ppm.

PREPARATION T

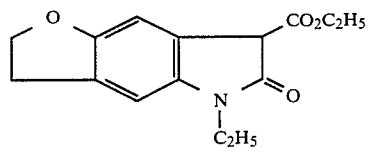

Ethyl 5-ethyl-6-oxo-2,3,6,7-tetrahydro-furo[2,3-f]indole-7-carboxylate

A mixture of 20 g. (73.3 mmoles) of ethyl 5-ethyl-6-oxo-6,7-dihydro-furo[2,3-f]indole-7-carboxylate and 4 g. of 10% palladium-on-carbon was shaken in a hydrogen atmosphere at an initial pressure of 50 psi. After 2 hours the catalyst was filtered and the filtrate evaporated. The residue was recrystallized from diethyl ether, 12.6 g. (63% yield), m.p. 82°–84° C.

Anal. Calcd. for C$_{15}$H$_{17}$NO$_4$: C, 65.4; H, 6.2; N, 5.1. Found: C, 65.4; H, 6.3; N, 5.1.

PREPARATION U

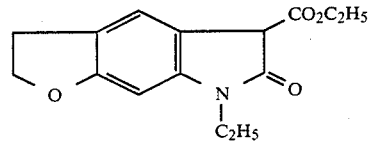

Ethyl 3-ethyl-4-oxo-4,5,7,8-tetrahydro-furo[3,2-f]indole-5-carboxylate

Employing the procedure of Preparation T, 7.55 (27.7 mmoles) of ethyl 3-ethyl-4-oxo-4,5-dihydro-furo[3,2-f]indole-5-carboxylate (Preparation E) and 1.5 g. of 10% palladium-on-carbon gave 4.54 g. (59% yield) of the titled intermediate, m.p. 78°–81° C.

Anal. Calcd. for C$_{15}$H$_{17}$NO$_4$: C, 65.4; H, 6.2; N, 5.1. Found: C, 65.4; H, 6.3; N, 5.0.

PREPARATION V

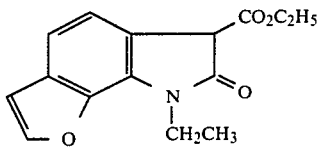

Ethyl 2-ethyl-3-oxo-3,4-dihydro-furo[3,2-g]indole-4-carboxylate

V1. O-(N-chloroacetyl-N-ethyl)anisidine

Using the procedure of Preparation G2, 100 g. (0.662 mole) of O-(N-ethyl)anisidine and 37.1 g. (0.331 mole) of chloroacetyl chloride gave a quantitative yield of the titled intermediate.

V2. 4- and 7-hydroxy-1-ethyloxindole

Employing the procedure of Preparation G3, 75.1 g. (0.331 mole) of O-(N-chloroacetyl-N-ethyl)anisidine and 133 g. (1.0 mole) of aluminum chloride gave a crude mixture of the titled compounds. The mixture was separated by chromatographing on 1 kg. of silica gel using diethyl ether-methylene chloride (1:1, v:v) as the eluent to give 5.24 g. (9% yield) of 7-hydroxy-1-ethyloxindole and 18.5 g. (32% yield) of the 4-hydroxy isomer.

The NMR (CDCl$_3$-DMSO-d$_6$) spectrum of the 7-hydroxy isomer showed absorption at 1.27 (t, J=7 Hz, CH$_3$), 3.4 (s, CH$_2$), 3.98 (q, J=7 Hz, NCH$_2$) and 6.72 (bs, ArH) ppm.

V3. 1-ethyl-7-chloroacetoxyoxindole

Following the procedure of Preparation A1, 4.7 g. (26.6 mmoles) of 1-ethyl-7-hydroxyoxindole and 5.99 g. (53.2 mmoles) of chloroacetyl chloride gave 5.3 g. (80% yield) of the titled compound, m.p. 105°–110° C.

The NMR (CDCl$_3$) spectrum showed absorption at 1.22 (t, J=7 Hz, CH$_3$), 3.51 (s, CH$_2$), 3.9 (q, J=7 Hz, NCH$_2$), 4.32 (s, CH$_2$Cl) and 6.9–7.2 (m, ArH) ppm.

V4. 1-ethyl-6-chloroacetyl-7-hydroxyoxindole

Following the procedure of Preparation A2, 5.33 g. (21.1 mmoles) of 1-ethyl-7-chloroacetoxyoxindole and 11.2 g. 84.3 mmoles) of aluminum chloride gave 2.17 g. (41% yield) of the titled intermediate, m.p. 161°–162° C.

Anal. Calcd. for C$_{12}$H$_{12}$ClNO$_3$: C, 56.8; H, 4.8; N, 5.5. Found: C, 56.9; H, 4.7; N, 5.5.

V5. 1-ethyl-6-(1-hydroxy-2-chloroethyl)-7-hydroxyoxindole and 2-ethyl-3-oxo-3,4-dihydro-furo[3,2-g]indole To a slurry of 2.0 g. (9.22 mmoles) of 1-ethyl-6-chloroacetyl-7-hydroxyoxindole in 100 ml. of methanol at 0° C. was added 378 mg. (9.95 mmoles) of sodium borohydride. The reaction was stirred for 40 minutes and then added to a saturated brine-methylene chloride mixture. The organic phase was separated and the aqueous acidified with 1N hydrochloric acid. The acidified aqueous was extracted with methylene chloride (2×75 ml.) and the organic phases combined and dried over magnesium sulfate. The oil remaining after removal of the solvent was dissolved in 32 ml. of acetonitrile, 0.5 ml. of a solution of 10% trifluoroacetic acid in acetonitrile was added, and the solution stirred 18 hours at 25° C. The reaction was evaporated to an oil, which was purified by chromatographing on 100 g. of silica gel using 50–100% diethyl ethermethylene chloride as the eluent, to give 430 mg. (27% yield) of 2-ethyl-3-oxo-3,4-dihydro-furo[3,2-g]indole and 830 mg. (41% yield) of 1-ethyl-6-(1-hydroxy-2-chloroethyl)-7-hydroxyoxindole, m.p. 141°–147° C.

The NMR (CDCl$_3$) of the latter compound showed absorption at 1.24 (t, J=7 Hz, CH$_3$), 3.37 (s, CH$_2$), 3.6–4.2 (m, NCH$_2$, CH$_2$Cl), 4.4 (d, J=2 Hz, OH), 4.98 (ddd, J=8,5 and 2 Hz, CH) and 6.62 (AB pattern, ArH) ppm.

V6. 2-ethyl-3-oxo-3,4,7,8-tetrahydro-7-hydroxyfuro[3,2-g]indole

To a solution of 800 mg. (3.14 mmoles) of 1-ethyl-6-(1-hydroxy-2-chloroethyl)-7-hydroxyoxindole in 10 ml. of tetrahydrofuran was added 478 ul (3.2 mmoles) of 1,8-diazabicyclo[5.4.0]undec-7-ene. After stirring for 15 minutes the reaction was added to a mixture of methylene chloride and 0.5N hydrochloric acid. The organic layer was separated, washed with a saturated sodium bicarbonate solution and dried over magnesium sulfate. Removal of the solvent gave 684 mg. (99% yield) of the title intermediate.

The NMR (CDCl$_3$-DMSO-d$_6$) spectrum showed absorption at 1.22 (t, J=7 Hz, CH$_3$), 3.50 (s, CH$_2$), 3.82 (q, J=7 Hz, NCH$_2$), 4.2–4.8 (m, CH$_2$O), 5.25 (m, CH), 5.52 (d, J=5 Hz, OH), 6.77 (d, J=8 Hz, ArH) and 7.01 (d, J=8 Hz, ArH) ppm.

V7. 2-ethyl-3-oxo-3,4-dihydro-furo[3,2-g]indole

Employing the procedure of Preparation B2, 648 mg. (2.96 mmoles) of 2-ethyl-3-oxo-3,4,7,8-tetrahydro-7-hydroxy-furo[3,2-g]indole gave 425 mg. (71% yield) of the desired intermediate, m.p. 149°–151° C.

Anal. Calcd. for C$_{12}$H$_{11}$NO$_2$: C, 71.6; H, 5.5; N, 7.0. Found: C, 71.3; H, 5.5; N, 6.9.

V8. ethyl 2-ethyl-3-oxo-3,4-dihydro-furo[3,2-g]indole-4-carboxylate

Using the procedure of Preparation C, 867 mg. (4.31 mmoles) of 2-ethyl-3-oxo-3,4-dihydro-furo[3,2-g]indole and 1.53 g. (12.9 mmoles) of diethylcarbonate gave 1.17 g. (100% yield) of the titled intermediate as an oil.

The NMR (CDCl$_3$) spectrum showed absorption at 1.2–1.7 (m, CH$_3$), 3.9–4.6 (m, NCH$_2$, OCH$_2$), 6.8 (m, ArH) and 7.2–7.7 (m, ArH) ppm.

PREPARATION W

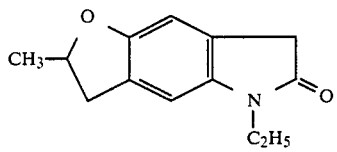

2-Methyl-5-ethyl-6-oxo-2,3,6,7-tetrahydrofuro[2,3-f]indole

W1. 1-ethyl-5-allyloxyoxindole

A mixture of 17.7 g. (0.1 mole) of 1-ethyl-5-hydroxyoxindole, 8.66 ml. (0.1 mole) of allyl bromide and 13.8 g. (0.1 mole) of potassium carbonate in 500 ml. of acetone was heated at reflux for 3 hours. The reaction was cooled, filtered and concentrated. The residue was purified by chromatographing on 550 g. of silica gel using diethyl ether-hexane (1:1, v:v) as the eluent to give 9.8 g. (45% yield) of the desired compound.

The NMR (CDCl$_3$) spectrum showed absorption at 1.24 (t, J=7 Hz, CH$_3$), 3.47 (s, CH$_2$), 3.79 (q, J=7 Hz, NCH$_2$), 4.5 (bd, J=5 Hz, OCH$_2$), 5.1–5.6 (m, vinyl H), 5.7–6.4 (m, vinyl H) and 6.6–7.0 (m, ArH) ppm.

W2. 1-ethyl-5-hydroxy-6-allyloxindole and 1-ethyl-4-allyl-5-hydroxyoxindole

A solution of 1.09 g. (5.02 mmoles) of 1-ethyl-5-allyloxyoxindole in 5 ml. of N,N-diethylaniline was heated at reflux for 1 hour. The cooled reaction was added to ice cold 1N hydrochloric acid and the mixture extracted with methylene chloride. The extract was washed with water (3×), saturated brine solution (1×) and dried over magnesium sulfate. The residue remaining after the solvent was removed was chromatographed on 22 g. of silica gel using 50–100% diethyl ether-hexane as the eluent to give 134 mg. (12% yield) of 1-ethyl-4-allyl-5-hydroxyoxindole and 644 mg. (59% yield) of 1-ethyl-5-hydroxy-6-allyloxindole, m.p. 130°–131° C.

The NMR (CDCl$_3$) spectrum of the latter compound showed absorption at 1.23 (t, J=7 Hz, CH$_3$), 3.32 (m, CH$_2$), 3.7 (q, J=7 Hz, NCH$_2$), 4.9–5.3 (m, vinyl H), 5.6–6.3 (m, vinyl H), 6.53 (s, ArH) and 6.8 (s, ArH) ppm.

W3. 2-methyl-5-ethyl-6-oxo-2,3,6,7-tetrahydrofuro[2,3-f]indole

To a solution of 6.0 g. (27.6 mmoles) of 1-ethyl-5-hydroxy-6-allyloxindole in 105 ml. of tetrahydrofuran was added 8.79 g. (27.6 mmoles) of mercuric acetate, and the reaction stirred for 1.5 hours. The mixture was diluted with 29 ml. of 3N sodium hydroxide solution followed by the addition of 522 mg. (13.7 mmoles) of sodium borohydride in 29 ml. of 3N sodium hydroxide solution. The mixture was stirred for 1 hour and was then diluted with diethyl ether and water. The organic phase was washed with water and a saturated brine solution, and then dried over magnesium sulfate. Evaporation of the solvent and chromatographing of the residue on 100 g. of silica gel, using diethyl ether-hexane (1:1, v:v) as the eluent, gave 1.68 g. (28% yield) of the desired product.

Acidification of the basic extract with hydrochloric acid followed by extraction with methylene chloride gave 2.91 g. (49%) of recovered starting material.

The NMR (CDCl$_3$) spectrum of the product showed absorption at 1.25 (t, J=7 Hz, CH$_3$), 1.48 (d, J=6 Hz, CH$_3$), 2.6–3.6 (m, CH$_2$), 3.42 (s, CH$_2$), 3.72 (q, J=7 Hz, NCH$_2$), 4.92 (sextet, J=7 Hz, CH) and 6.67 (bs, ArH) ppm.

PREPARATION X

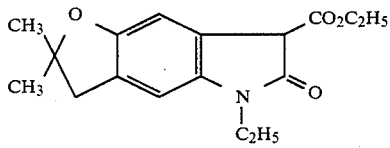

Ethyl 2,2-dimethyl-5-ethyl-6-oxo-2,3,6,7-tetrahydro-furo[2,3-f]indole-7-carboxylate X1. 1-ethyl-5-(2-methyl-2-propenyloxy)oxindole Using the procedure of Preparation W1, 10.8 g. (61 mmoles) of 1-ethyl-5-hydroxyoxindole and 11.1 g. (61 mmoles) of 1-iodo-2-methyl-2-propene gave 8 g. (57% yield) of the titled intermediate.

The NMR (CDCl$_3$) spectrum showed absorption at 1.22 (t, J=7 Hz, CH$_3$), 1.82 (s, vinyl CH$_3$), 3.4 (s, CH$_2$), 3.71 (q, J=7 Hz, NCH$_2$), 4.38 (s, OCH$_2$), 5 (m, vinyl H), 6.7 (s, ArH, OH) and 6.84 (s, ArH) ppm.

X2. 1-ethyl-5-hydroxy-6-(2-methyl-2-propenyl)oxindole and 1-ethyl-4-(2-methyl-2-propenyl)-5-hydroxyoxindole Employing the procedure of Preparation W2, 6.7 g. (29 mmoles) of 1-ethyl-5-(2-methyl-2-propenyl)oxindole gave 4.7 g. (70% yield) of 1-ethyl-5-hydroxy-6-(2-methyl-2-propenyl)oxindole, m.p. 118°–120° C. and 740 mg. (11% yield) of 1-ethyl-4-(2-methyl-2-propenyl)-5-hydroxyoxindole.

The NMR (CDCl$_3$) spectrum of the former compound showed absorption at 1.22 (t, J=7 Hz, CH$_3$), 1.76 (bs, CH$_3$), 3.32 (s, CH$_2$), 3.4 (s, CH$_2$), 3.65 (q, J=7 Hz, NCH$_2$), 4.85 (m, vinyl H), 5.72 (s, OH), 6.49 (s, ArH) and 6.72 (s, ArH) ppm.

X3. 2,2-dimethyl-5-ethyl-6-oxo-2,3,6,7-tetrahydrofuro[2,3-f]indole

A solution of 231 mg. (1. mmole) of 1-ethyl-5-hydroxy-6-(2-methyl-2-propenyl)oxindole and 190 mg. (1. mmole) of p-toluenesulfonic acid monohydrate in 1 ml. of methylene chloride was stirred at 25° for 18 hours. The reaction was diluted with methylene chloride and washed with 1N sodium hydroxide solution, water and a saturated brine solution. The organic phase was separated, dried and concentrated to give a quantitative yield of the desired intermediate.

The NMR (CDCl$_3$) spectrum showed absorption at 1.22 (t, J=7 Hz, CH$_3$), 1.49 (s, CH$_3$), 3.02 (s, CH$_2$), 3.44 (s, CH$_2$), 3.72 (q, J=7 Hz, NCH$_2$) and 6.63 (ArH) ppm.

X4. ethyl 2,2-dimethyl-5-ethyl-6-oxo-2,3,6,7-tetrahydro-furo[2,3-f]indole-7-carboxylate To a slurry of 26.4 mg. (1.1 mmoles) of sodium hydride in 2 ml. of benzene was added 231 mg. (1 mmole) of 2,2-dimethyl-5-ethyl-6-oxo-2,3,6,7-tetrahydrofuro[2,3-f]indole and the resultant reaction mixture stirred for 5 minutes. To the reaction mixture was added 0.13 ml. (1.1 mmoles) of diethyl carbonate, and the mixture allowed to stir 18 hours. The reaction is then added to methylene chloride and 4N hydrochloric acid, and the organic phase separated, washed with water and a saturated brine solution and dried over magnesium sulfate. The extract was subsequently treated with 1N sodium hydroxide solution and the basic layer separated. The aqueous basic layer was acidified and the product extracted with methylene chloride. The organic phase was separated, dried with magnesium sulfate and concentrated to give 155 mg. (51% yield) of the titled intermediate as an oil.

The NMR (CDCl$_3$) spectrum showed absorption at 1.22 (bt, J=7 Hz, CH$_3$), 1.49 (s, CH$_3$), 3.0 (bs, CH$_2$), 3.69 (q, J=7 Hz, NCH$_2$), 4.19 (bq, J=7 Hz, OCH$_2$), 4.25 (s, CH), 6.6 and 6.9 (s, ArH) and 6.7 and 7.05 (s, ArH) ppm.

PREPARATION Y

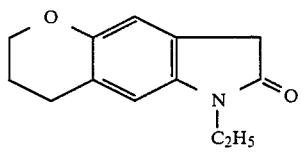

1-Ethyl-2-oxo-2,3-dihydro-pyrano[2,3-f]indole

Y1. 1-ethyl-5-hydroxy-6-(3-hydroxypropyl)oxindole

To a solution of 3.0 g. (13.8 mmoles) of 1-ethyl-5-hydroxy-6-allyloxindole (Preparation W2) in 30 ml. of tetrahydrofuran at 0° C. was slowly added 13.8 ml. (13.8 mmoles) of a 1M borane-tetrahydrofuran solution. The reaction was stirred for 30 minutes followed by the addition of 50 ml. of 1N sodium hydroxide solution and 25 ml. of a 30% hydrogen peroxide solution. After stirring the reaction for 5 minutes it was acidified with 25 ml. of 4N hydrochloric acid and extracted with methylene chloride (10×50 ml.). The extracts were combined, dried and concentrated to give the crude product, which was purified by chromatographing on 120 g. of silica gel using 5% methanol-methylene chloride as the eluent to give 1.85 g. (56% yield) of the desired product.

The NMR (CD$_3$OD) spectrum showed absorption at 1.22 (t, J=7 Hz, CH$_3$), 1.82 (bp, J=7 Hz, CH$_2$), 2.70 (bt, J=7 Hz, CH$_2$), 3.2–4.0 (m, CH$_2$), 6.68 (s, ArH) and 6.72 (s, ArH) ppm.

Y2. 1-ethyl-5-hydroxy-6-(3-tosyloxypropyl)oxindole

To a solution of 1.8 g. (7.66 mmoles) of 1-ethyl-5-hydroxy-6-(3-hydroxypropyl)oxindole in 18 ml. of pyridine cooled to 0° C. was added 1.46 g. (7.66 mmoles) of p-tosyl chloride, and the reaction mixture allowed to stir for 20 hours at 0° C. The reaction was added to cold, dilute hydrochloric acid, and the mixture extracted with methylene chloride. The organic phase was washed with 4N hydrochloric acid and a saturated brine solution, and dried over magnesium sulfate. Removal of the solvent gave 2.02 g. (70% yield) of the titled intermediate.

The NMR (CDCl$_3$) spectrum showed absorption at 1.22 (t, J=7 Hz, CH$_3$), 1.98 (bp, J=7 Hz, CH$_2$), 2.41 (s, CH$_3$), 2.70 (bt, J=7 Hz, CH$_2$), 3.4 (s, CH$_2$), 3.68 (q, J=7 Hz, NCH$_2$), 4.04 (t, J=6 Hz, OCH$_2$), 6.52 (s, ArH), 6.78 (s, ArH), 7.29 (d, J=8 Hz, ArH) and 7.71 (d, J=8 Hz, ArH) ppm.

Y3. 1-ethyl-2-oxo-2,3-dihydro-pyrano[2,3-f]indole

A mixture of 1.65 g. (4.41 mmoles) of 1-ethyl-5-hydroxy-6-(3-tosyloxypropyl)oxindole and 610 mg. (4.41 mmoles) of potassium carbonate in 90 ml. of acetone was heated at reflux for 2.5 hours. The reaction was cooled, filtered and the filtrate evaporated. The crude residue was purified by chromatographing on 100 g. of silica gel, using 66% diethyl ether-hexane as the eluent, to give 571 mg. (60% yield) of the desired intermediate.

The NMR (CDCl$_3$) spectrum showed absorption at 1.22 (t, J=7 Hz, CH$_3$), 1.7–2.2 (m, CH$_2$), 2.79 (t, J=6 Hz, CH$_2$), 3.41 (s, CH$_2$), 3.68 (q, J=7 Hz, NCH$_2$), 4.11 (d, J=5 Hz, CH$_2$), 6.43 (s, ArH) and 6.69 (s, ArH) ppm.

PREPARATION Z

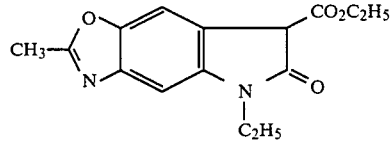

Ethyl 2-methyl-5-ethyl-6-oxo-6,7-dihydrooxazolo[5,4-f]indole-7-carboxylate

Z1. 1-ethyl-5-hydroxy-6-nitrooxindole

To a stirred solution of 40 ml. of conc. sulfuric acid at 0° C. was added 4.0 g. (22.6 mmoles) of 1-ethyl-5-hydroxyoxindole and the stirring continued for 30 minutes. The temperature was lowered to −30° C. and 1.6 ml. (24.9 mmoles) of fuming nitric acid and 16 ml. of conc. sulfuric acid was added dropwise over a 1 hour period. The cold (−30° C.) reaction mixture was treated with ice water and methylene chloride. The organic phase was separated, dried and concentrated to a solid, which was purified by filtering through 50 g. of silica gel (containing 20 g. of water) with methylene chloride. Evaporation of the filtrate gave 2.4 g. (48% yield) of the desired intermediate, m.p. 167°–169° C.

The NMR (250 MHz, CDCl$_3$) spectrum showed absorption at 1.32 (t, J=7 Hz, CH$_3$), 3.6 (s, CH$_2$), 3.81 (q, J=7 Hz, NCH$_2$), 7.15 (bs, ArH), 7.43 (s, ArH) and 10.79 (s, OH) ppm.

Z2. 1-ethyl-5-hydroxy-6-aminooxindole hydrochloride

A mixture of 222 mg. (1. mmole) of 1-ethyl-5-hydroxy-6-nitrooxindole and 20 mg. of 10% palladium-on-carbon in 50 ml. of ethanol was shaken in a hydrogen atmosphere at an initial pressure of 40 p.s.i. After 45 minutes the catalyst was filtered and the filtrate concentrated to a small volume, and the residue added to 200 ml. of diethyl ether saturated with hydrogen chloride. The resulting precipitate was filtered and dried, 200 mg. (88% yield).

Z3. 2-methyl-5-ethyl-6-oxo-6,7-dihydro-oxazolo[5,4-f]indole

A mixture of 761 mg. (3.34 mmoles) of 1-ethyl-5-hydroxy-6-aminooxindole hydrochloride and 1.8 ml. (10 mmoles) of triethylorthoacetate was heated 10 minutes at 75° C. The reaction was cooled, diluted with methylene chloride and washed twice with water. Concentration of the dried organic phase gave the crude poduct which was recrystallized from toluenehexane, 515 mg. (72% yield).

The NMR (CDCl$_3$) spectrum showed absorption at 1.29 (t, J=7 Hz, CH$_3$), 2.6 (s, CH$_3$), 3.52 (s, CH$_2$), 3.76 (q, J=7 Hz, NCH$_2$), 6.98 (s, ArH) and 7.27 (s, ArH)

Z4. ethyl 2-methyl-5-ethyl-6-oxo-6,7-dihydro-oxazolo[5,4-f]indole-7-carboxylate

Following the procedure of Preparation C, 515 mg. (2.38 mmoles) of 2-methyl-5-ethyl-6-oxo-6,7-dihydrooxazolo[5,4-f]indole and 0.87 ml. (7.2 mmoles) of diethyl carbonate gave 337 mg. (49% yield) of the titled intermediate.

The NMR (CDCl$_3$) spectrum showed absorption at 1.25 (bt, J=7 Hz, CH$_3$), 2.6 (s, CH$_3$), 3.79 (q, J=7 Hz, NCH$_2$), 4.18 (q, J=7 Hz, OCH$_2$), 4.4 (bs, CH), 6.99 (s, ArH) and 7.4 (s, ArH) ppm.

I claim:

1. Compounds of the formulae

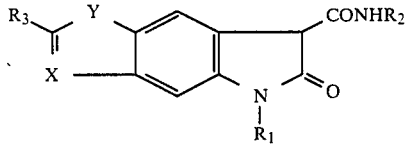

and

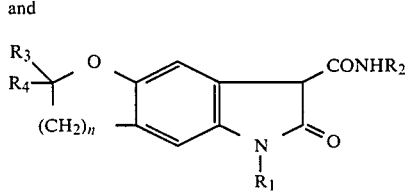

and the pharmaceutically acceptable base salts thereof, wherein Y is selected from the group consisting of oxygen and sulfur; X is selected from the group consisting of N, CH and C(CH$_3$);

R$_1$ is selected from the group consisting of alkyl containing one to three carbon atoms and phenyl; R$_2$ is selected from the group consisting of phenyl, monosubstituted phenyl wherein said substituent is selected from the group consisting of fluoro, chloro, trifluoromethyl, methylthio, methoxy, acetyl, ethoxycarbonyl and methylsulfinyl, disubstituted phenyl wherein said substituents are each selected from fluoro and methoxy, and heterocyclic and mono- and dimethyl substituted heterocyclic wherein said heterocyclic is selected from the group consisting of 2-thiazolyl, 2-oxazolyl, 5-isothiazolyl, 3-isoxazolyl, benzothiazolyl, 2-thiazolinyl, 2-thiadiazolyl, 2-pyrimidinyl and pyridyl; R$_3$ and R$_4$ are each selected from the group consisting of hydrogen and methyl; and n is an integer of 1 or 2.

2. A compound of claim 1, formula 1.

3. A compound of claim 2, wherein Y is oxygen, X is CH, R$_3$ is hydrogen and R$_1$ is alkyl containing one to three carbon atoms.

4. The compound of claim 3, wherein R$_1$ is ethyl and R$_2$ is 2-thiazolyl.

5. The compound of claim 3, wherein R$_1$ is ethyl and R$_2$ is 4-methyl-2-thiazolyl.

6. The compound of claim 3, wherein R$_1$ is ethyl and R$_2$ is 4-fluorophenyl.

7. The compound of claim 3, wherein R$_1$ is ethyl and R$_2$ is 5-methyl-2-thiazolyl.

8. A compound of claim 2, wherein Y is sulfur, X is CH, R$_3$ is hydrogen and R$_1$ is alkyl containing one to three carbon atoms.

9. The compound of claim 8, wherein R$_1$ is ethyl and R$_2$ is 5-methyl-2-thiazolyl.

10. A compound of claim 1, formula 2.

11. A compound of claim 10, wherein R$_1$ is alkyl containing from one to three carbon atoms, R$_3$ and R$_4$ are each hydrogen and n is 1.

12. The compound of claim 11, wherein R$_1$ is ethyl and R$_2$ is 4-fluorophenyl.

13. A method of treating an inflammatory disease in a mammalian subject, which comprises administering to said mammalian subject an antiinflammatory disease treating amount of a compound of claim 1.

14. Compounds of the formulae

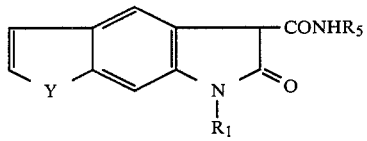

3 and

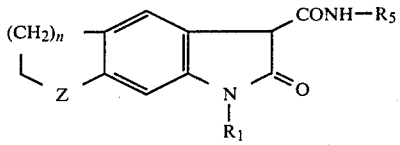

4 and the pharmaceutically acceptable base salts thereof, wherein Y is selected from the group consisting of oxygen and sulfur; R$_1$ is selected from the group consisting of alkyl containing from one to three carbon atoms and phenyl; Z is selected from the group consisting of oxygen and methylene; n is an integer of 1 or 2; and R$_5$ is selected from the group consisting of phenyl, fluorophenyl, difluorophenyl, chlorophenyl, pyridyl, 2-thiazolyl and monomethyl-2-thiazolyl.

15. A compound of claim 14, formula 3.

16. A compound of claim 15, wherein Y is oxygen and R$_1$ is alkyl containing from one to three carbon atoms.

17. The compound of claim 16, wherein R$_5$ is 5-methyl-2-thiazolyl and R$_1$ is ethyl.

18. The compound of claim 16, wherein R$_5$ is 2-thiazolyl and R$_1$ is ethyl.

19. A compound of claim 15, wherein Y is sulfur and R$_1$ is alkyl containing from one to three carbon atoms.

20. The compound of claim 19, wherein R$_5$ is 5-methyl-2-thiazolyl and R$_1$ is ethyl.

21. A method of treating an inflammatory disease in a mammalian subject, which comprises administering to said mammalian subject an antiinflammatory disease treating amount of a compound of claim 14.

22. The compound of the formula

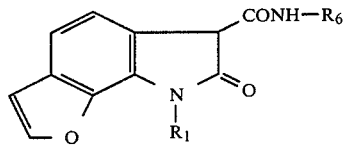

and the pharmaceutically acceptable base salt thereof, wherein R$_1$ is selected from the group consisting of alkyl containing from one to three carbon atoms and phenyl; and R$_6$ is selected from the group consisting of fluorophenyl, difluorophenyl, pyridyl, 2-thiazolyl and 5-methyl-2-thiazolyl.

23. A compound of claim 22, wherein R$_1$ is alkyl containing from one to three carbon atoms.

24. The compound of claim 23, wherein R$_6$ is 5-methyl-2-thiazolyl.

25. A method of treating an inflammatory disease in a mammalian subject, which comprises administering to said mammalian subject an antiinflammatory disease treating amount of a compound of claim 22.

* * * * *